(12) United States Patent
Jain

(10) Patent No.: US 10,428,370 B2
(45) Date of Patent: Oct. 1, 2019

(54) UNIVERSAL METHOD FOR EXTRACTING NUCLEIC ACID MOLECULES FROM A DIVERSE POPULATION OF ONE OR MORE TYPES OF MICROBES IN A SAMPLE

(71) Applicant: Sun Genomics, Inc., San Diego, CA (US)

(72) Inventor: Suneer Jain, San Diego, CA (US)

(73) Assignee: Sun Genomics, Inc., San Diego, CA (US)

( * ) Notice: Subject to any disclaimer, the term of this patent is extended or adjusted under 35 U.S.C. 154(b) by 0 days.

(21) Appl. No.: 15/824,754

(22) Filed: Nov. 28, 2017

(65) Prior Publication Data

US 2018/0080065 A1  Mar. 22, 2018

Related U.S. Application Data

(63) Continuation of application No. PCT/US2017/051849, filed on Sep. 15, 2017.

(60) Provisional application No. 62/412,787, filed on Oct. 25, 2016, provisional application No. 62/395,316, filed on Sep. 15, 2016.

(51) Int. Cl.
| | |
|---|---|
| *G01N 33/48* | (2006.01) |
| *C12Q 1/6806* | (2018.01) |
| *C12Q 1/686* | (2018.01) |
| *C12Q 1/6827* | (2018.01) |
| *A61K 35/741* | (2015.01) |
| *G16B 20/00* | (2019.01) |
| *A61K 35/00* | (2006.01) |
| *C12Q 1/689* | (2018.01) |

(52) U.S. Cl.
CPC ........ *C12Q 1/6806* (2013.01); *A61K 35/741* (2013.01); *C12Q 1/686* (2013.01); *C12Q 1/6827* (2013.01); *G16B 20/00* (2019.02); *A61K 2035/115* (2013.01); *C12Q 1/689* (2013.01)

(58) Field of Classification Search
None
See application file for complete search history.

(56) References Cited

U.S. PATENT DOCUMENTS

| 4,652,517 A | 3/1987 | Scholl |
| 4,652,630 A | 3/1987 | Bentle |
| (Continued) | | |

FOREIGN PATENT DOCUMENTS

| WO | WO 2017/044880 A1 | 3/2017 |
| WO | WO 2017/070123 A1 | 4/2017 |

OTHER PUBLICATIONS

Gill et al. (Science, 2006, 312, June 1355-1359).*

(Continued)

*Primary Examiner* — Larry D Riggs, II
(74) *Attorney, Agent, or Firm* — DLA Piper LLP (US)

(57) ABSTRACT

Disclosed herein are methods of extracting genetic material from a diverse population of one or more types of microbes in a sample. Microbes can be prokaryotes or eukaryotes and may include bacteria, archaea, fungi, protozoa, helminths, parasites, viruses, phages, and others. Extraction may be from a single sample and subsequent identification may be through a molecular method such as qPCR, PCR, RFLP, SSCP, allele specific PCR, targeted sequencing, pull down sequencing, whole shotgun sequencing, or other methods.

20 Claims, 16 Drawing Sheets
(16 of 16 Drawing Sheet(s) Filed in Color)

(56) References Cited

U.S. PATENT DOCUMENTS

| | | | |
|---|---|---|---|
| 5,075,430 | A | 12/1991 | Little |
| 5,155,018 | A | 10/1992 | Gillespie |
| 5,234,809 | A | 8/1993 | Boom |
| 5,350,679 | A | 9/1994 | Hess |
| 6,180,778 | B1 | 1/2001 | Bastian |
| 7,683,035 | B1 | 3/2010 | Erbacher |
| 2002/0001829 | A1 | 1/2002 | Lee et al. |
| 2005/0164260 | A1 | 7/2005 | Chen |
| 2006/0173165 | A1 | 8/2006 | Faison |
| 2006/0204978 | A1 | 9/2006 | Nilsen et al. |
| 2007/0015177 | A1 | 1/2007 | Maron |
| 2008/0264842 | A1 | 10/2008 | Hukari |
| 2011/0130558 | A1 | 6/2011 | Ritt |
| 2012/0021421 | A1* | 1/2012 | Amar ............... C12Q 1/6883 435/6.12 |
| 2013/0079251 | A1 | 3/2013 | Boles |
| 2013/0165635 | A1 | 6/2013 | Kim |
| 2013/0338350 | A1 | 12/2013 | Hurt, Jr. et al. |
| 2014/0212868 | A1 | 7/2014 | Wilmes et al. |
| 2015/0225712 | A1 | 8/2015 | Gunther et al. |
| 2015/0355178 | A1 | 12/2015 | Myatt |
| 2016/0115471 | A1 | 4/2016 | Kim |
| 2017/0343455 | A1 | 11/2017 | Middleton |
| 2018/0080065 | A1 | 3/2018 | Jain |

OTHER PUBLICATIONS

Rapley, R., (Basic Techniques in Molecular Biology, Medical Biomethods Handbook, Humana Press, 1-12).*
Delzenne et al. (Targeting gut microbiota in obesity: effects of prebiotics and probiotics; Nat. Rev., Endocrinol., 2011, 1-8).*
International Search Report dated Jan. 18, 2018, regarding PCT/US2017/051849.
Protein Solubilization, Jun. 12, 2015, 3 pages; http://www.bio-rad.com/en-us/applications-technologies/protein-solubilization.
Sarkosyl (Molecular Biology) Jan. 5, 2015, 2 pages; http://what-when-how.com/molecular-biology/.
Cano et al.: "Revival and Identification of Bacterial spores in 25- to 40-Million-Year-Old Dominican Amber"; Science, May 1995, vol. 268, pp. 1060-1064.
ConsumerLab.com: "Some Surprising Results from Tests of 43 probiotic supplements and Kefir drinks", Nov. 6, 2015, pp. 1-3.
Eckberg et al.: "Diversity of the Human Intestinal Microbial Flora"; Science, Jun. 10, 2005, vol. 308, pp. 1635-1639.
Guarner et al.: "WGO Guidelines regarding Probiotics and Prebiotics"; J. of Clinical Gastroenterology, Jul. 2012, 46(6) : 468-481.
Inceoglu et al.: "Effect of DNA Extraction Method on the Apparent Microbial Diversity of Soil"; Applied and Environmental Microbiology, May 2010, 76 (10), pp. 3378-3382.
Laflamme et al.: "Flow cytometry analysis of germinating Bacillus spores, using membrane potential dye"; Arch. Microbiology, 2005, vol. 183, pp. 107-112.
Luo et al.: "Direct Comparisons of Illumina vs. Roche 454 Sequencing Technologies on the Same Microbial Community DNA Sample"; Plos One, Feb. 2012, 7(2): e30087, 12 pgs.
Mwamburi et al. "Effect of surfactants and temperature on germination and vegetative growth of Beauveria bassiana"; Brazilian J. of Microbiology, 2015, 46(1): 67-74.
Schabereiter-Gurtner et al.: "Evaluation of a protocol for molecular broad-range diagnosis of culture-negative bacterial infections in clinical routine diagnosis"; J. of Applied Microbiology, 2007, vol. 104, pp. 1228-1237.
Wikipedia: "Metagenomics" 2018, entry downloaded Sep. 13, 2018, 18 pgs.
International Search Report dated Jun. 19, 2019, regarding PCT/US2019/025457.

* cited by examiner

FIG. 9

| | UNIQUE SPECIES IN DATABASE |
|---|---|
| ARCHAEA | 676 |
| BACTERIA | 94,641 |
| FUNGI | 238 |
| PROTOZOA | 79 |
| VIRUSES | 7,497 |
| TOTAL | 103,131 |

FIG. 10

UNIVERSAL METHOD FOR EXTRACTING NUCLEIC ACID MOLECULES FROM A DIVERSE POPULATION OF ONE OR MORE TYPES OF MICROBES IN A SAMPLE

CROSS REFERENCE TO RELATED APPLICATIONS

This application is a continuation application of International Application No. PCT/US2017/051849 filed Sep. 15, 2017, now pending, which claims the benefit under 35 U.S.C. § 119(e) to U.S. Application Ser. No. 62/412,787 filed Oct. 25, 2016 and to U.S. Application Ser. No. 62/395,316 filed Sep. 15, 2016, both now expired. The disclosure of each of the prior applications is considered part of and is incorporated by reference in the disclosure of this application.

BACKGROUND OF THE INVENTION

Field of Invention

The present invention relates generally to genomic analysis and more particularly to a method of extracting and analyzing nucleic acid molecules from a diverse population of microbes in a biological sample.

Background Information

About 100 trillion microorganisms live in and on the human body vastly outnumbering the body's approximately 10 trillion human cells. These normally harmless viruses, bacteria and fungi are referred to as commensal or mutualistic organisms. Commensal and mutualistic organisms help keep our bodies healthy in many ways. Together all of the microorganisms living in and on the body—commensal, mutualistic and pathogenic—are referred to as the microbiome and their equilibrium and associated metabolome is closely linked to an individual's health status and vice-versa.

Advances in nucleic acid sequencing has created an opportunity to quickly and accurately identify and profile the microbiome inhabiting the gut and subcutaneous tissue. The optimal flora also interacts with the host immune system in a synergistic way further propagating its health benefits. The associated metabolome of individuals can also be profiled either by a mass-spectrometry based system or using genomics-based metabolome modeling and flux-balance analysis and used to make a healthy metabolome profile. All these methodologies can be used to dissect the complexity of microbial communities.

SUMMARY OF THE INVENTION

The present invention is directed to a method of extracting nucleic acid molecules from a diverse population of microbes in a biological, environmental, dietary supplement, or other ecological microbial organism heterogeneous populations sample and use of nucleic acid or extracts through processing steps and analysis for the determination of probiotic customization to an individual. Processing steps specific to this invention include, RNA or DNA clean-up, fragmentation, separation, or digestion; library or nucleic acid preparation for downstream applications, such as PCR, qPCR, digital PCR, or sequencing; preprocessing for bioinformatic QC, filtering, alignment, or data segregation; metagenomics or human genomic bioinformatics pipeline for microbial species taxonomic assignment; and other organism alignment, identification, and variant interpretation.

Accordingly, in one aspect, the invention provides a method for preparing a sample for analysis. The method includes: a) mixing the sample with a first lysis solution comprising a detergent, e.g., SDS, and a chelator, e.g., EDTA; b) adding a second lysis solution having a lysozyme to the mixture of step a); and c) adding a third lysis solution comprising a chaotropic agent, e.g., urea, lithium acetate, guanidine hydrochloride, and the like, to the mixture of step b). Pre-processing steps may include physical lysis may be used to further optimize nucleic acid yield. Examples of mechanical lysis include sonication, bead mixing, and bead mill homogenization.

In another aspect, the invention provides a method of monitoring a probiotic treatment of a subject. The method includes:

extracting genetic material from any microbes present in a first sample obtained from the subject, said genetic material extracted according to any one of claims 0 to 0;

subjecting the genetic material extracted from the first sample to metagenomics analysis;

treating the subject with a probiotic and then extracting genetic material from any microbes present in a second sample obtained from the subject in the same manner as the extraction of genetic material from the first sample;

performing metagenomics analysis on the extracted genetic material from the second sample; and comparing the results of the metagenomics analysis of the first sample with the metagenomics analysis of the second sample.

In yet another aspect, the invention provides a method comprising calculating a probiotic score from probiotic organisms detected in a gut with or without additional chemistry or genetic tests.

In still another aspect, the invention provides a method comprising calculating a score for a microbiome, the score being used to assess if the microbiome is in dysbiosis, neutral, or stable.

The invention further provides a computing system comprising: a memory; and one or more processors coupled to the memory, the one or more processors configured to perform operations to perform a method of the present invention.

The invention also provides an automated platform for performing a method of the invention.

The invention provides an all-in-one method for extracting nucleic acids from a diverse flora of microbes from a biological, environmental, dietary supplement, or other ecological microbial organism heterogeneous populations sample.

In embodiments, the invention may be used in determining composition and relative abundance of microbes, via analyzing their respective nucleic acids, in probiotics and environmental samples. DNA is purified and used downstream for nucleic acid analysis (notably metagenomics analysis where genome of more than one species/subspecies is identified).

Both the foregoing general description and the following detailed description are exemplary and explanatory only and are intended to provide further explanation of the invention as claimed. Any accompanying drawings are included to provide a further understanding of the invention and are incorporated in and constitute part of this specification, illustrate several embodiments of the invention, and together with the description serve to explain the principles of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9 is a table setting forth organisms identified via the method of the invention from a dietary supplement mixed culture.

FIG. 10 is a table setting forth the classification of unique species of various microbes stored in the database of the invention.

DETAILED DESCRIPTION OF THE INVENTION

Figure 1:
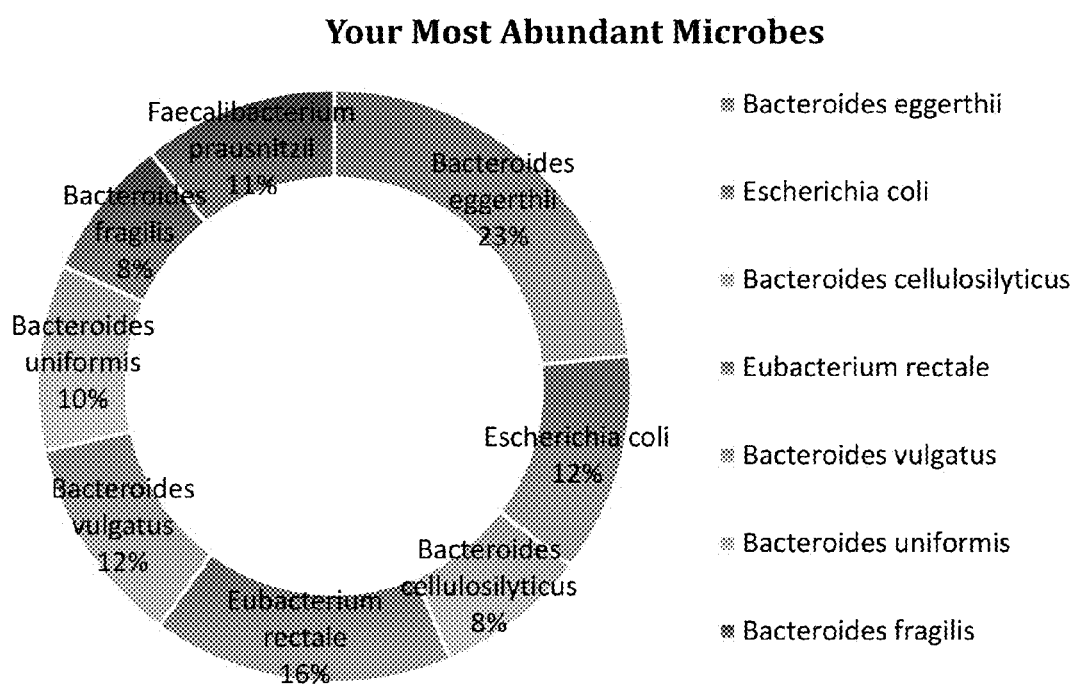
FIG. 1 is a schematic diagram illustrating the presence of high prevalence organisms of a microbiome signature of a human (high protein diet, >50 years old, supplement user).
Figure 2A:
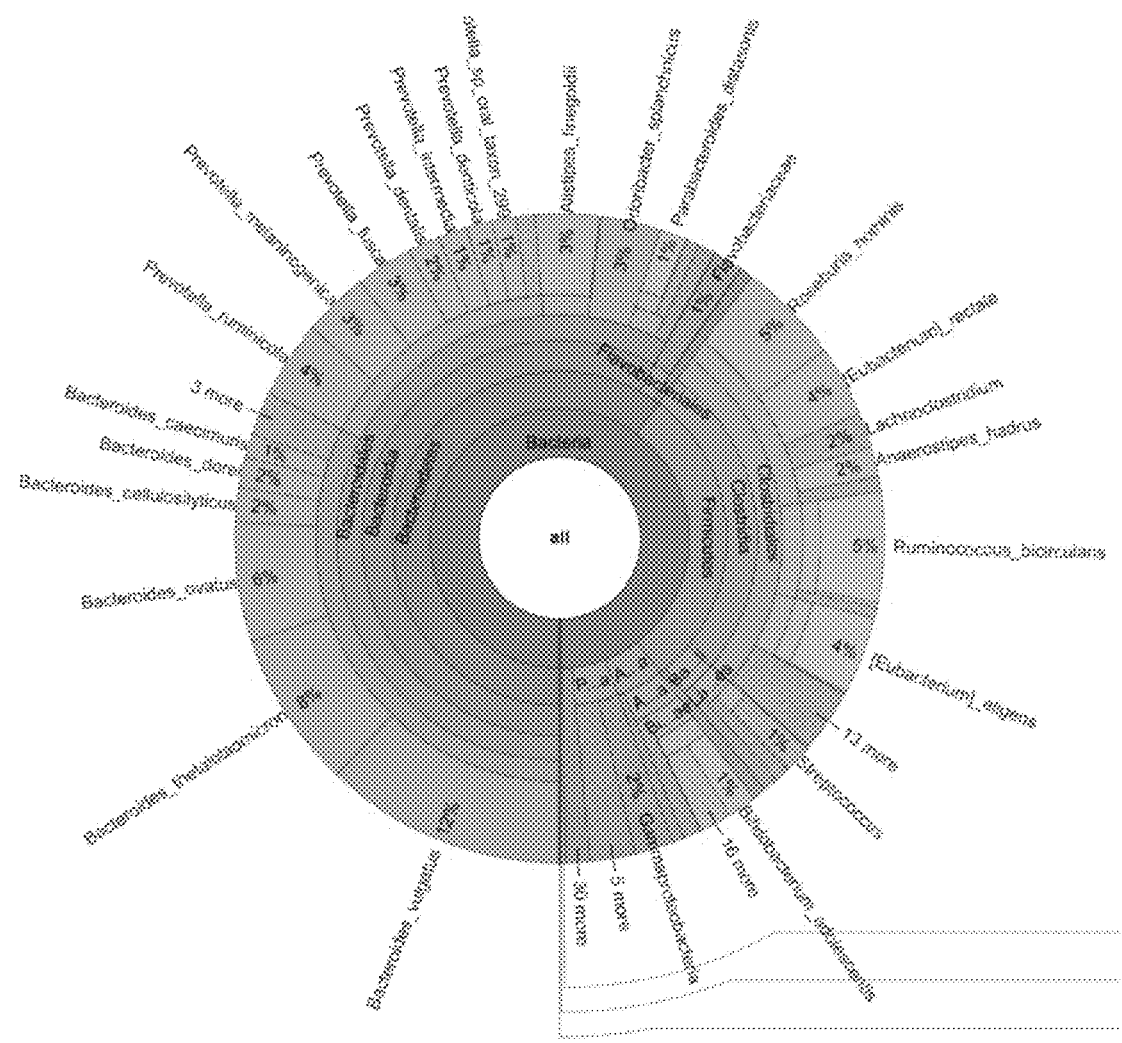
FIG. 2A is a schematic diagram illustrating the presence of high prevalence organisms (bacteria) of a microbiome signature of a human (high carbohydrate diet, 18-50 years old, vegetarian diet).
Figure 2B:
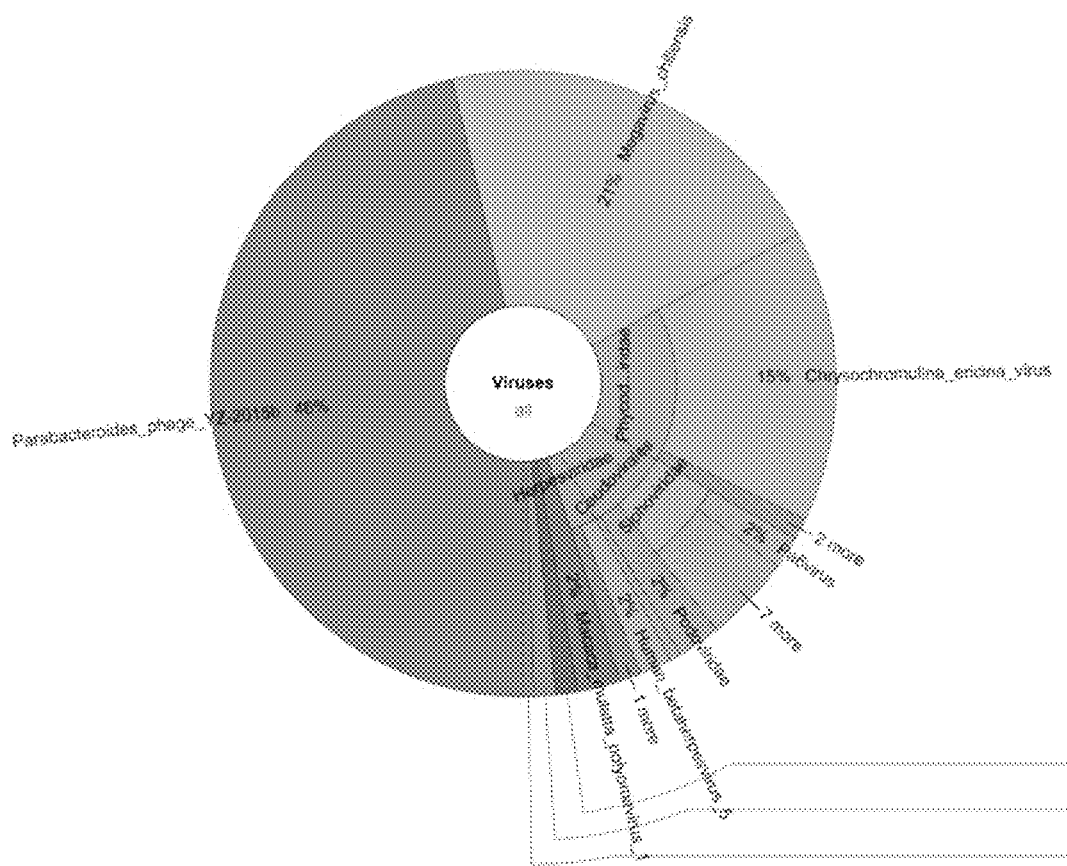
FIG. 2B is a schematic diagram illustrating the presence of high prevalence organisms (viruses and phages) of a microbiome signature of a human (high carbohydrate diet, 18-50 years old, vegetarian diet).
Figure 2C:
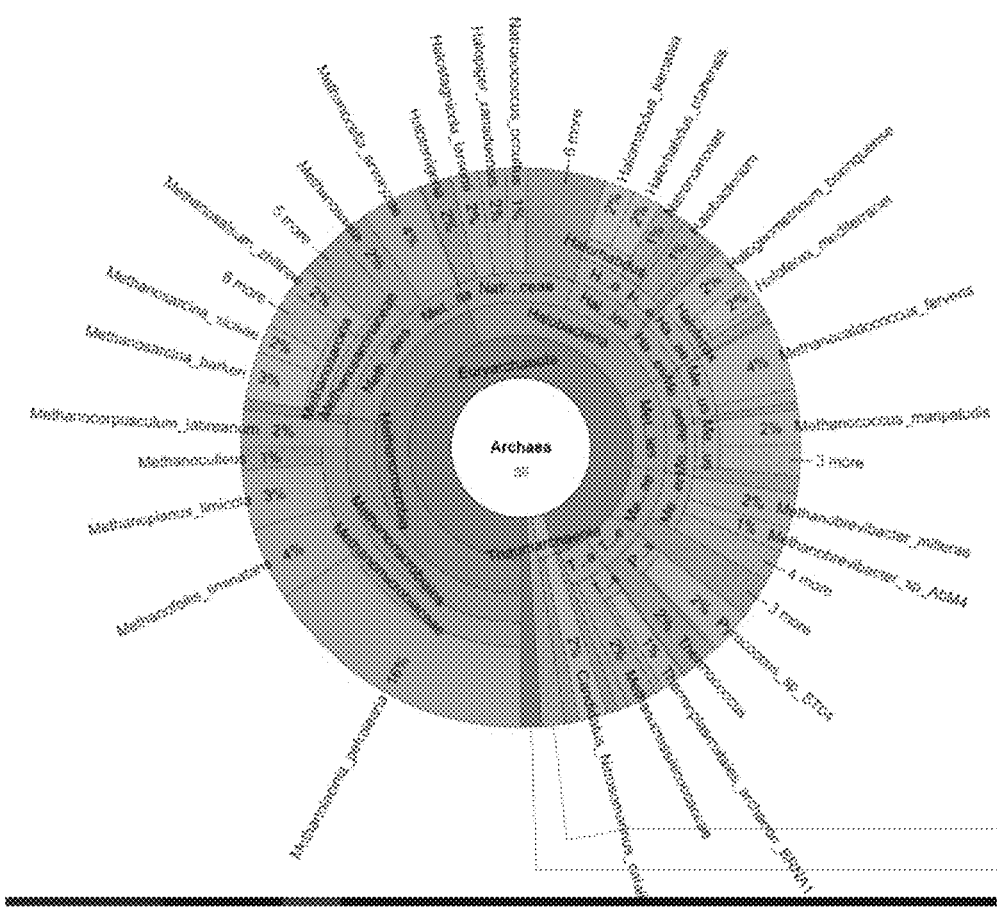
FIG. 2C is a schematic diagram illustrating the presence of high prevalence organisms (archaea) of a microbiome signature of a human (high carbohydrate diet, 18-50 years old, vegetarian diet).
Figure 2D:
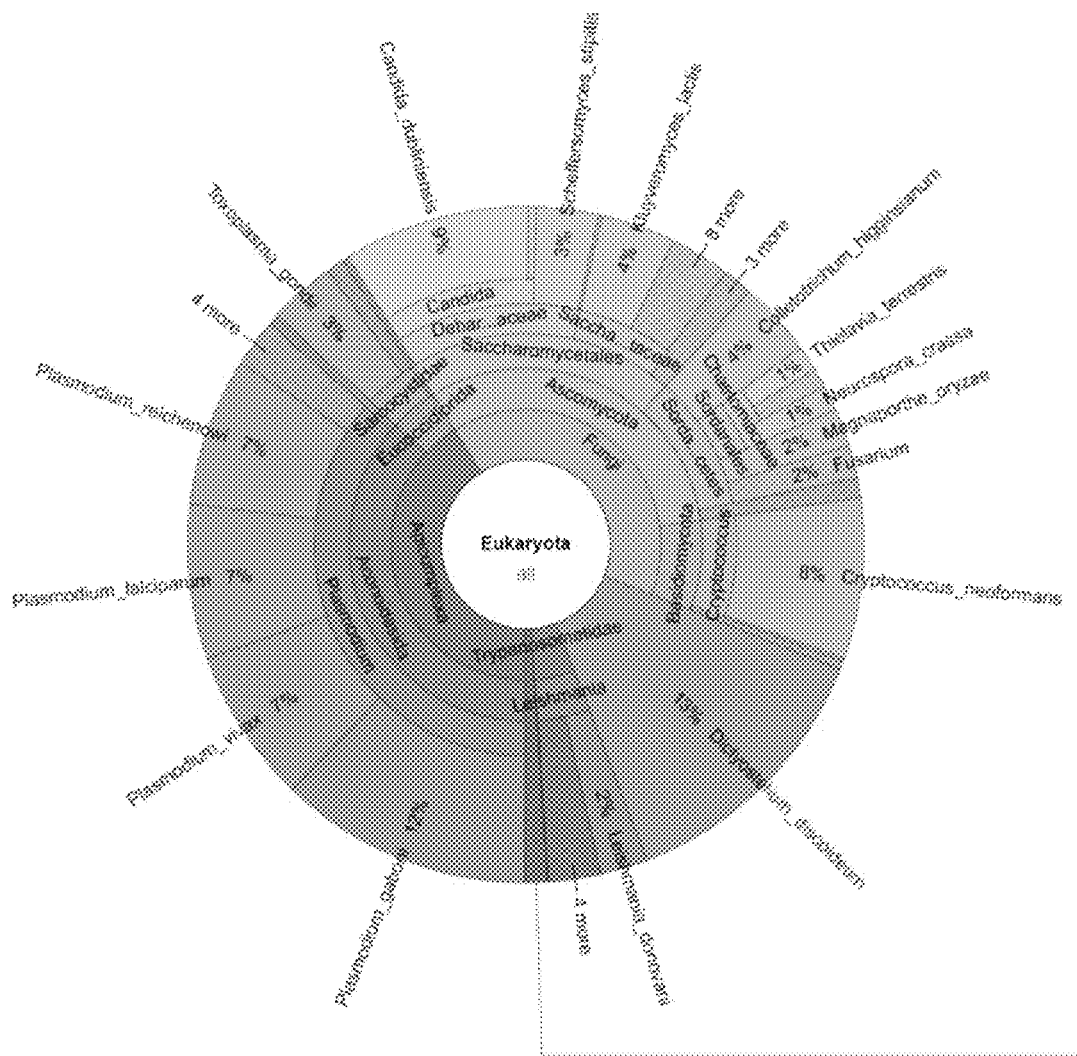
FIG. 2D is a schematic diagram illustrating the presence of high prevalence organisms (fungi and other eukaryotes) of a microbiome signature of a human (high carbohydrate diet, 18-50 years old, vegetarian diet).
Figure 3A:
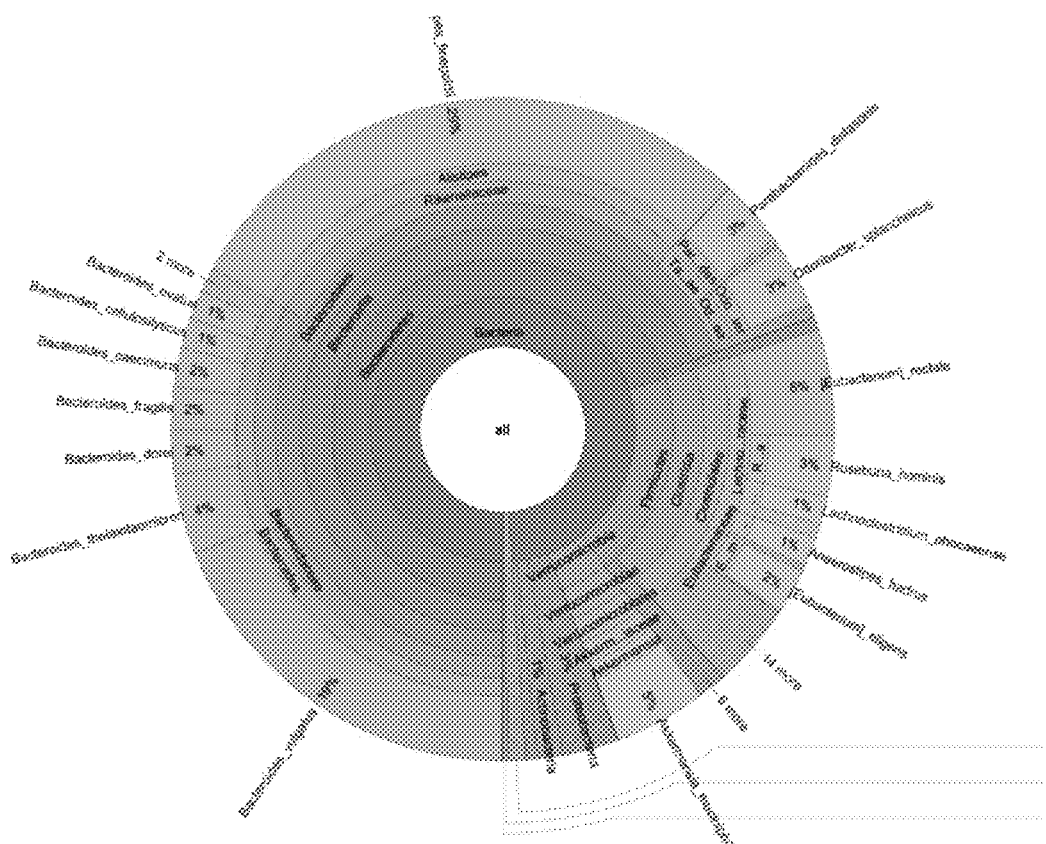
FIG. 3A is a schematic diagram illustrating the presence of high prevalence organisms (bacteria) of a microbiome signature of a human (high carbohydrate diet, 18-50 years old, non-vegetarian diet).
Figure 3B:
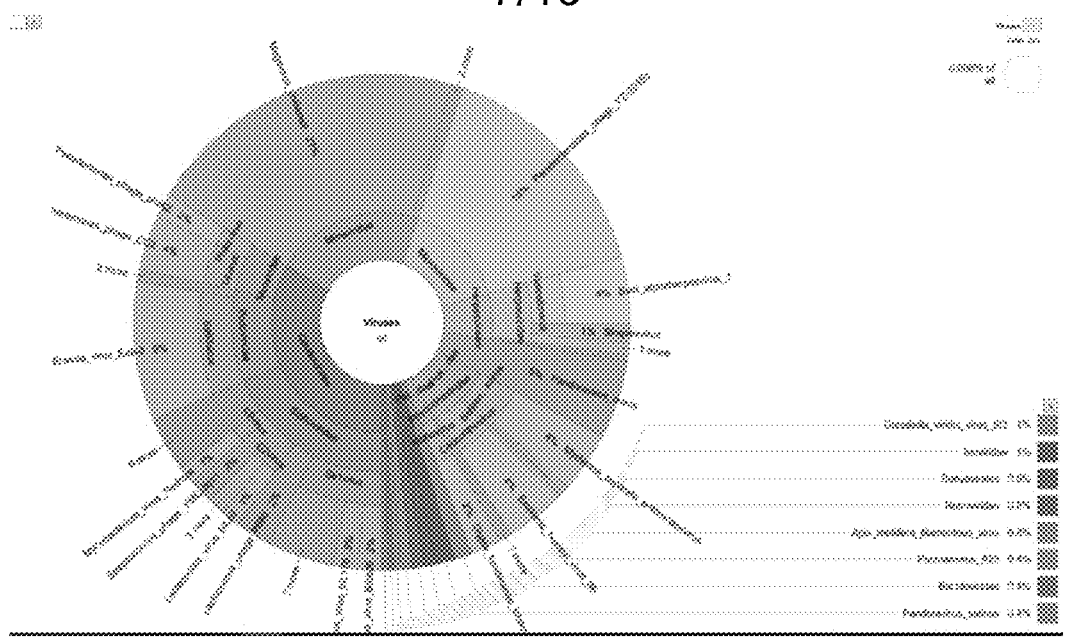
FIG. 3B is a schematic diagram illustrating the presence of high prevalence organisms (viruses and phages) of a microbiome signature of a human (high carbohydrate diet, 18-50 years old, non-vegetarian diet).
Figure 3C:
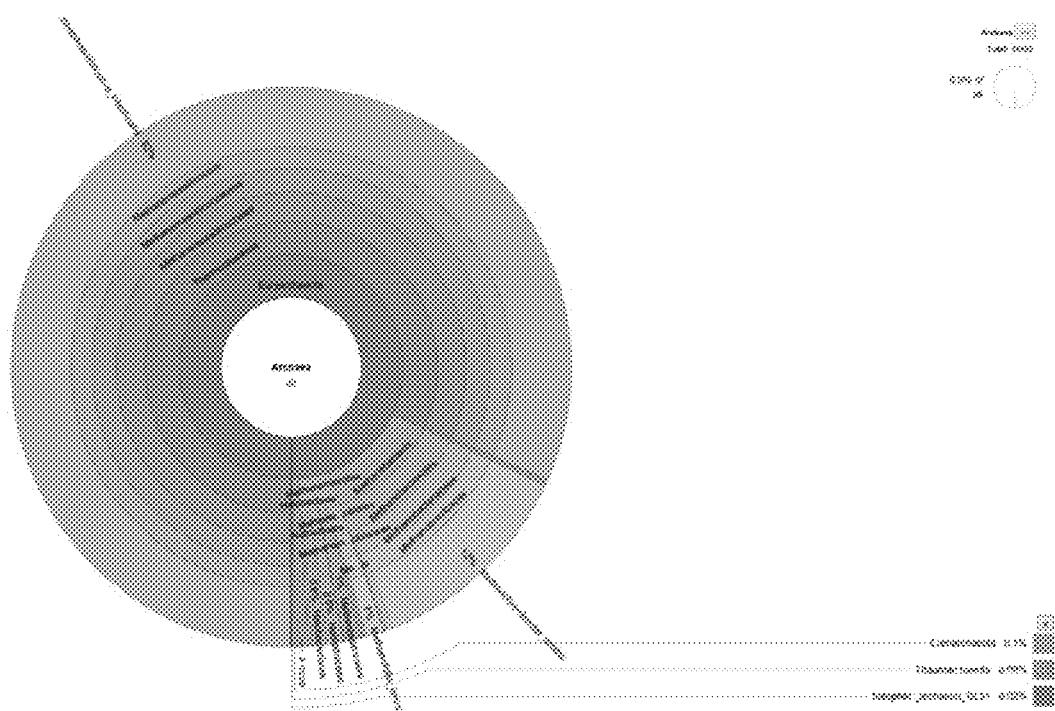
FIG. 3C is a schematic diagram illustrating the presence of high prevalence organisms (archaea) of a microbiome signature of a human (high carbohydrate diet, 18-50 years old, non-vegetarian diet).
Figure 3D:
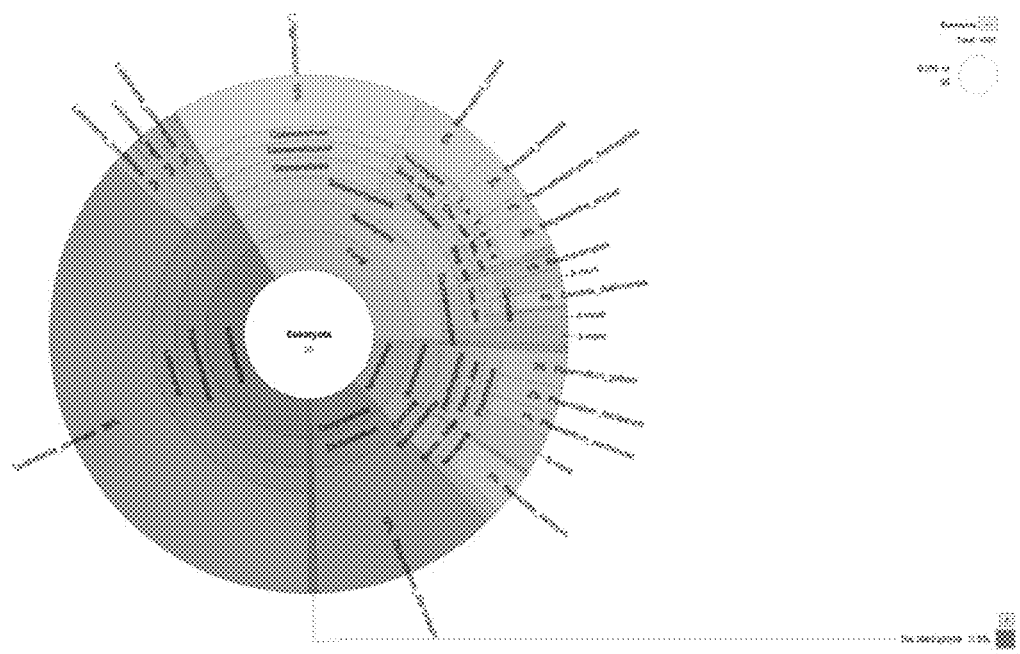
FIG. 3D is a schematic diagram illustrating the presence of high prevalence organisms (fungi and other eukaryotes) of a microbiome signature of a human (high carbohydrate diet, 18-50 years old, non-vegetarian diet).
Figure 4A:
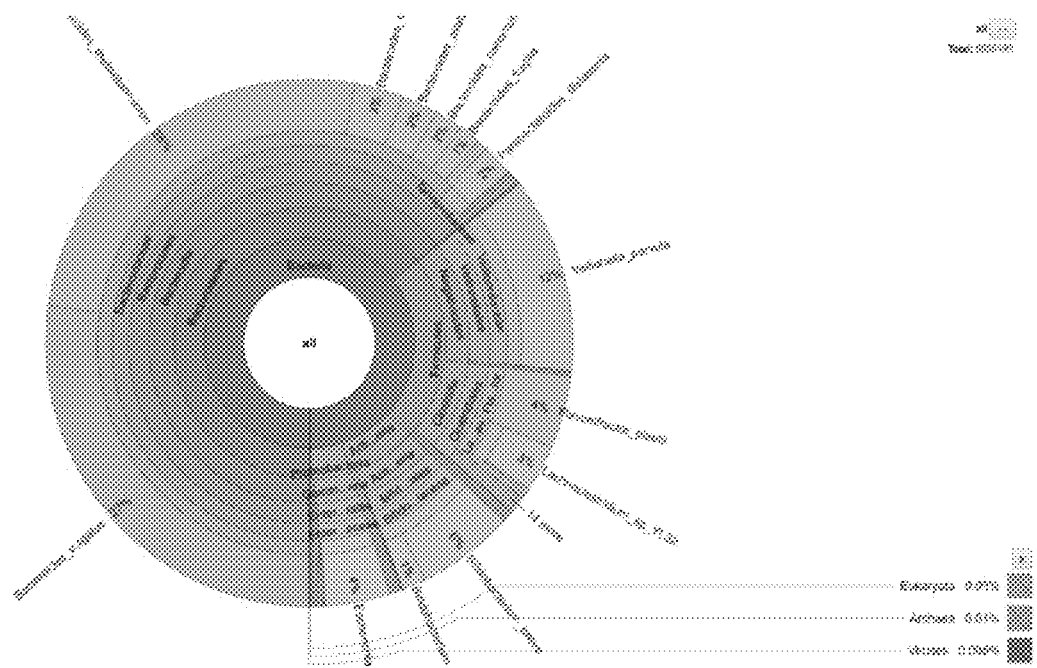
FIG. 4A is a schematic diagram illustrating the presence of high prevalence organisms (bacteria) of a microbiome signature of a human (high dairy protein diet, 0-2 years old, vegetarian non-nursing).
Figure 4B:
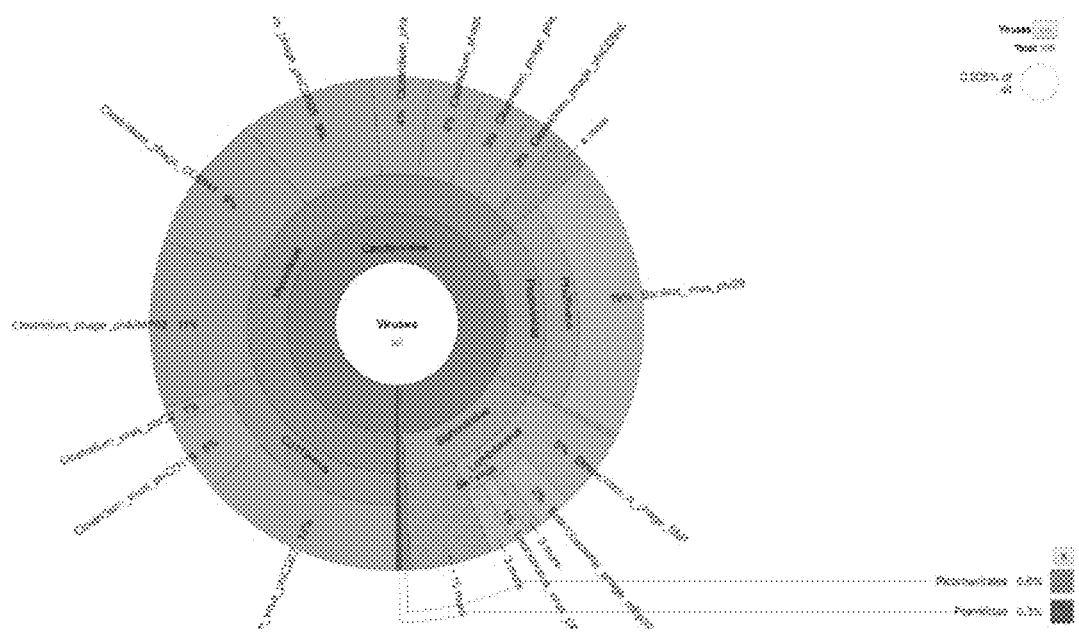
FIG. 4B is a schematic diagram illustrating the presence of high prevalence organisms (viruses and phages) of a microbiome signature of a human (high dairy protein diet, 0-2 years old, vegetarian non-nursing).
Figure 4C:
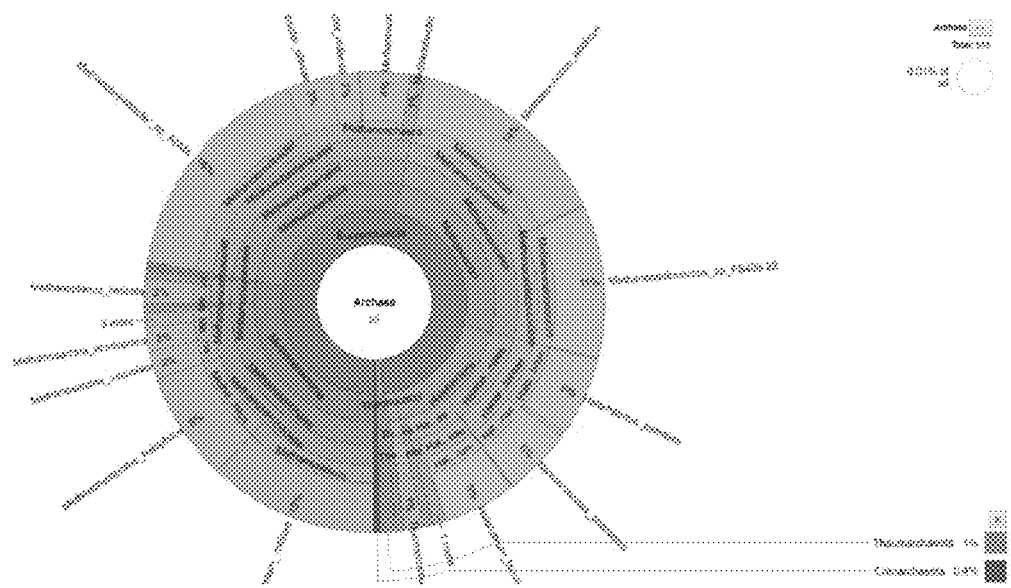
FIG. 4C is a schematic diagram illustrating the presence of high prevalence organisms (archaea) of a microbiome signature of a human (high dairy protein diet, 0-2 years old, vegetarian non-nursing).
Figure 4D:
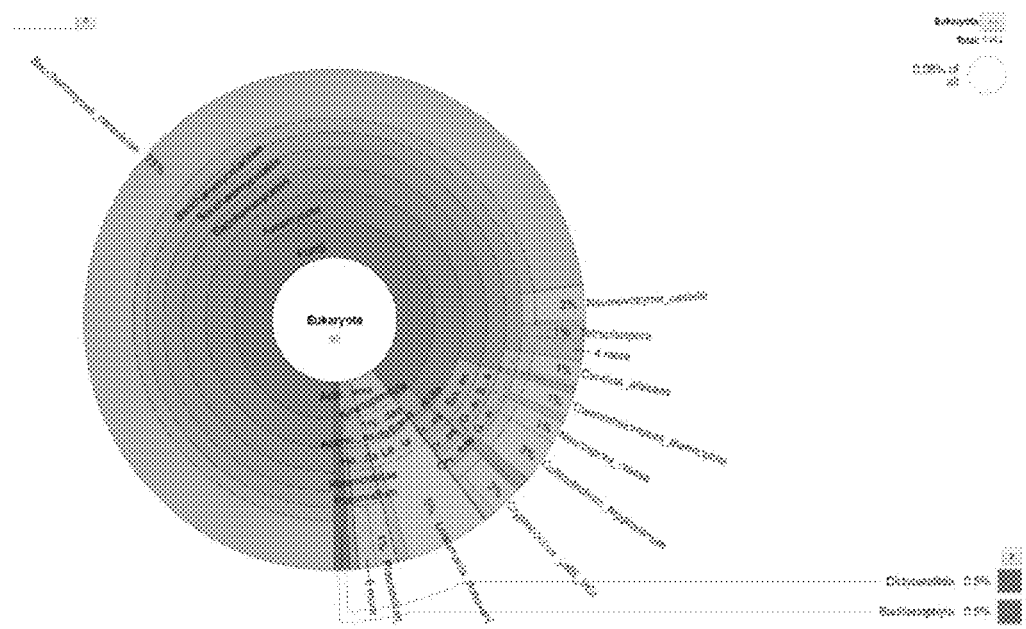
FIG. 4D is a schematic diagram illustrating the presence of high prevalence organisms (fungi and other eukaryotes) of a microbiome signature of a human (high dairy protein diet, 0-2 years old, vegetarian non-nursing).
Figure 5:
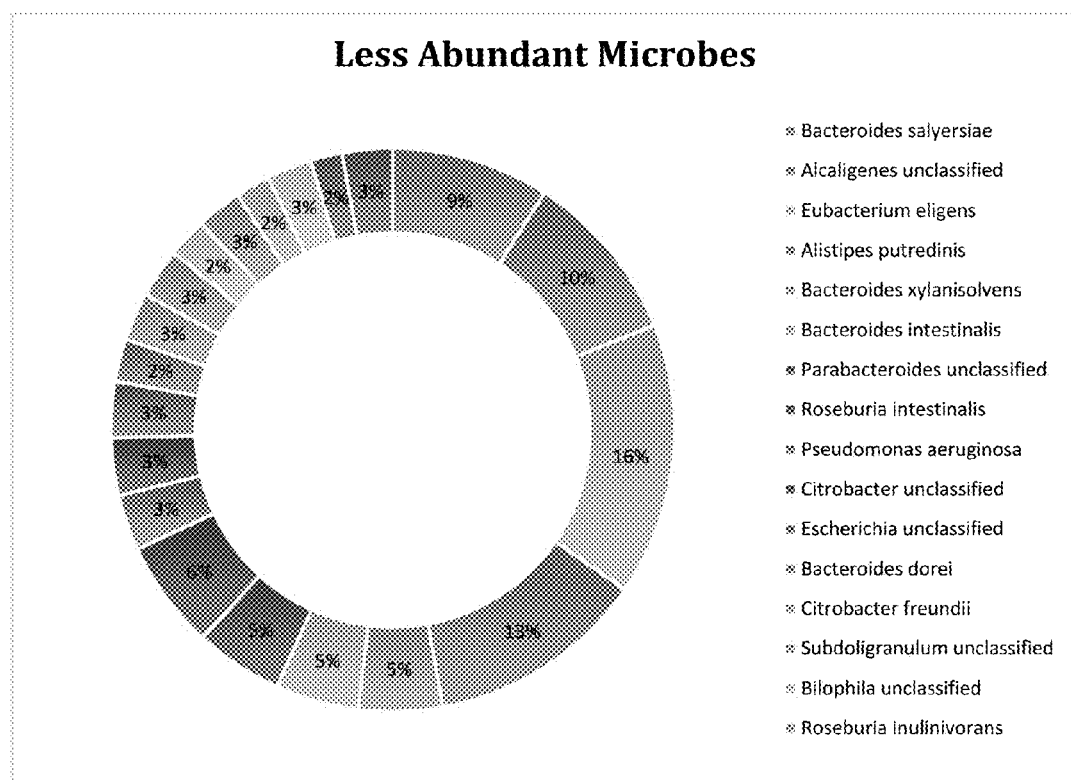
FIG. 5 is a schematic diagram illustrating the presence lower prevalent organisms and identification of opportunistic pathogens of a microbiome signature of a human.
Figure 6:
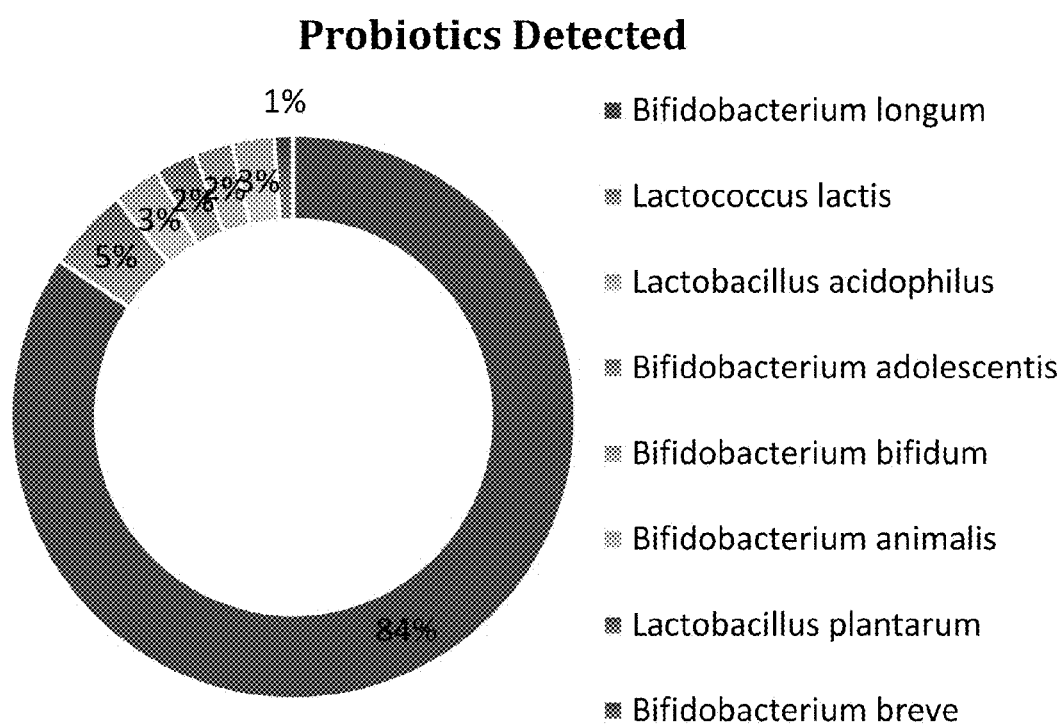
FIG. 6 is a schematic diagram illustrating typical probiotics detected in a microbiome signature of a human.
Figure 7:
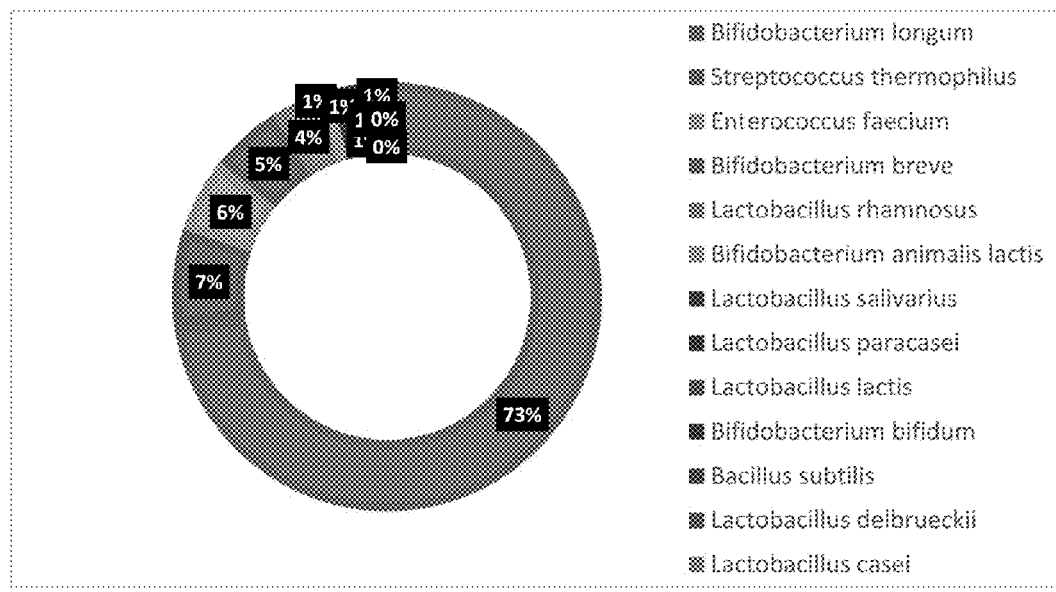
FIG. 7 is a schematic diagram illustrating typical probiotics detected in a microbiome signature of a human.
Figure 8:
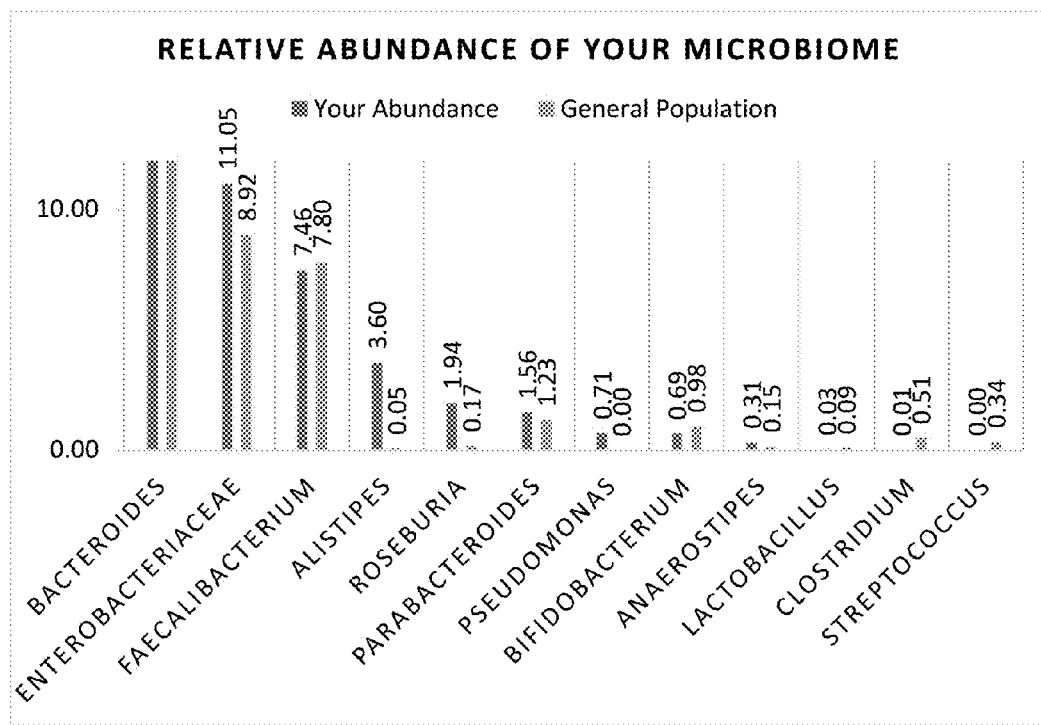
FIG. 8 is a schematic graphical plat illustrating showing comparison of individual relative abundance to database average for normal population.

The present invention provides a universal method for extracting nucleic acid molecules from a diverse population of one or more types of microbes in a sample. The types of microbes include: gram-positive bacteria, gram-positive bacterial spores, gram-negative bacteria, archaea, protozoa, helminths, algae, fungi, fungal spores, viruses, viroids, bacteriophages, and rotifers. In some embodiments, the diverse population is a plurality of different microbes of the same type, e.g., gram-positive bacteria. In some embodiments, the diverse population is a plurality of different types of microbes, e.g., bacteria (gram-positive bacteria, gram-positive bacterial spores and/or gram-negative), fungi, viruses, and bacteriophages.

Because different types of microbes have different compositions and mechanisms to protect their own genetic material it is often difficult to extract the genetic material from one type of microbe without compromising the ability to also extract the genetic material of another type of microbe in the same biological sample. The present invention, however, allows the extraction of genetic material from different types of microbes in a sample without sacrificing the amount of genetic material that can be obtained from one type of microbe by extracting the genetic material of another type of microbe in the same sample. According to the present invention, the sample comprising the microbes may be a biological sample, environmental sample, an artificially created sample (e.g., a laboratory test or control sample, a sample of a probiotic composition or supplement, etc.), or the like. Examples of biological samples include tissue samples, blood samples, plasma samples, cerebrospinal fluid samples, urine samples, fecal samples, samples of material obtained from the digestive tract, biological secretions (e.g., semen, vaginal secretions, breast milk, tears, saliva, etc.), and the like. Solid samples may be liquefied or mixed with a solution, and then genetic material of the microbes present in the liquefied sample, mixture, or solution obtained from the mixture may be extracted in accordance with the present invention. The extracted genetic material may be subjected to further processing and analysis such as purification, amplification, and sequencing.

In some embodiments, the extracted genetic material is subjected to metagenomics analysis to, for example, identify the one or more types of microbes in the sample from which the genetic material was extracted. In additional embodiments, full whole genome shotgun sequencing can be performed on prepared extracted nucleic acid material from human fecal samples. Preparations include nucleic acid clean up reactions to remove organic solvents, impurities, salts, phenols, and other process inhibiting contaminants. Additional preparations include nucleic acid library prep from each sample where the gDNA is subject to modifications and/or amplifications to prep the sample for sequencing on a sequencing platform such as massively parallel sequencing by synthesis, nanopore, long read, and/or CMOS electronic, sequencing methods.

As disclosed herein, the inventive method allows the successful extraction of genetic material from one or more different types of microbes present in the same sample by subjecting the microbes to three different compositions in a particular order. The method according to the present invention comprises first lysing any gram-negative bacteria present in the sample, which is followed by digesting the polysaccharide component of the cell walls of any yeast and bacteria present in the sample, and then disrupting any cell walls that are intact after the second step with a chaotropic agent.

Briefly, the first step comprises mixing the sample with a first lysis solution comprising a detergent (e.g., sodium dodecyl sulfate (SDS)) and a chelator (e.g., ethylenediaminetetraacetic acid (EDTA)) to lyse any gram-negative bacteria present in the sample. The first lysis solution may further include one or more buffers (e.g., Tris), one or more mild detergents (e.g., Triton X-100), and/or one or more proteases (e.g., proteinase K).

After the first step, the sample is mixed with a second lysis solution comprising a lysozyme to digest the polysaccharide component of any yeast and bacterial cell walls present in the mixture. Because lysozyme may inhibit the activity of the first lysis solution, it is important that contact of the sample with the second lysis solution occurs after treating the sample with the first lysis solution.

After treatment with the second lysis solution, a third lysis solution comprising a chaotropic agent (e.g., urea, lithium acetate, guanidine hydrochloride, etc.) is added to the mixture to disrupt any cell walls that are not digested by the second lysis solution. The third lysis solution may include a detergent such as SDS.

In some embodiments, both the first lysis solution and the third lysis solution comprise SDS at a working concentration of between 1-10% w/v. In some embodiments, after treatment with the third lysis solution, the mixture is further treated with a fourth lysis solution comprising a chaotropic agent (e.g., urea, lithium acetate, guanidine hydrochloride, etc.) and Proteinase K. In some embodiments where the chaotropic agent of the third lysis solution is lithium acetate, the mixture is then subjected to heat shock treatment and may then be treated with the fourth lysis solution.

In some embodiments, if the sample has or is suspected of having bacterial and/or fungal spores, the sample may be subjected to a pretreatment step that induces germination of the cell walls of the spores before contact with the first lysis solution. The pretreatment step may comprise mixing the sample with a chemical such as a mild detergent, e.g., Tween-80, to induce germination or cultivating the sample under conditions (e.g., temperature) that induce germination. In some embodiments, where germination is induced with a chemical, the chemical is preferably one that does not inhibit, reduce, or modify the activity or effectiveness of the first, second, and third lysis solutions.

In some embodiments, the method according to the present invention may further include one or more mechanical treatment steps that cause physical lysis by mechanical methods including sonication, bead mixing, bead mill homogenization, pressurization, microfluidization, and the like. In some embodiments, a mechanical treatment step is performed before subjecting the sample to the first lysis solution.

The method according to the present invention is capable of extracting nucleic acid molecules from a variety of microbes including yeast (i.e., *Saccharomyces* spp.), gram-negative bacteria (e.g., *Acinetobacter* spp.), gram-positive bacteria (e.g., *Bifidobacterium* spp.), viruses (e.g., *Sclerotinia* spp.), spores (*Bacillus* spp.) Helminths (tapeworm *Echinococcus* spp.), Protozoa (Sarcodina—the ameba, e.g., *Entamoeba*) and phages (e.g., *Lactobacillus* phages).

The following examples are intended to illustrate but not to limit the invention.

Extraction Method

A range of 10 mg to 5000 mg of sample were added to a sterile 2 milliliters (mL) micro centrifuge tube. Bead beating may optionally be performed by adding 400 microliters (μL) of bead pure mixture and vortexing for about 30 seconds at 8000 rpm. If, however, high-molecular weight nucleic acids, e.g., genomic DNA, are desired to be obtained, bead beating is preferably avoided.

First Lysis Solution Treatment Step

To lyse any gram-negative bacteria in the sample, the sample was subjected to a First Lysis Solution by adding about 400 μL of Digestion Buffer (1% w/v SDS, 25 mM Tris HCl, 2.5 mM EDTA, 1% trident-x 100, pH 8) and about 20 μL of Proteinase K to the sample and gently mixed. The mixture was then incubated for about 30 minutes at 55° C.

Second Lysis Solution Treatment Step

To lyse any gram-positive bacteria in the sample, a Second Lysis Solution comprising a glucoside hydrolase ("lysozyme") was added to the mixture obtained from the First Lysis Solution Treatment Step to give a final lysozyme concentration of 1 mg/mL and a pH of about 8.0. Suitable glucoside hydrolases may be obtained from a variety of sources including egg whites, tears, or mucus or saliva of various animals. The mixture was then incubated for a period of about 1 to 24 hours at 37° C.

Third Lysis Solution Treatment Step

To lyse any fungal and/or yeast cells present in the sample, a Third Lysis Solution comprising 1M lithium acetate in distilled sterile H2O and 5% w/v SDS was added to obtain about a 1:5 dilution of the mixture resulting from the Second Lysis Solution Treatment Step. The treated mixture was incubated for 15 minutes at 70° C. followed by heat shock at 95° C. for one minute and then brought to room temperature by placing in a 22° C. water bath.

As the Second and Third Lysis Solution Treatment Steps are sufficient to lyse the outer coats of bacteriophages and viruses, no additional step is needed for extracting the genetic material from bacteriophages and viruses that may be present in the sample.

Nucleic Acid Purification

The genetic material extracted from the lysed microbes, i.e., the nucleic acid molecules present in the mixture after being subjected to the First, Second, and Third Lysis Solution Treatment Steps were then purified to DNA and RNA purification by splitting the mixture into two microcentifuge tubes. DNA was extracted from one tube by adding about 20 μL RNAse A and incubating for 5 minutes at room temperature. The mixture was run through a biopolymer tissue homogenizer column. If bead beating was previously performed, subjecting the mixture to the tissue homogenizer column is preferably avoided.

The eluate was then centrifuged at 1000 g for 5 minutes. The supernatant was treated with about 400 μL of DNA Lysis Solution (Guanidine HCl, Tris-EDTA, and 70% EtOH) and about 20 μL of Proteinase K, mixed, and then incubated at 55° C. for 10 minutes. Then EtOH at −22° C. was added and the mixture was mixed by inverting. The mixture may be subjected to one or more additional DNA extraction and purification methods known in the art.

RNA was extracted from the second microcentrifuge tube by running the mixture through a biopolymer tissue homogenizer column. Again, if bead beating was previously performed, subjecting the mixture to the tissue homogenizer column is preferably avoided. The eluate was then centrifuged at 1000 g for 5 minutes. The supernatant was treated with about 40 µL DNase I (1 U) in a solution of 25 mM MgCl2 and then incubated at 37° for about 15 minutes. Then the mixture was subjected to acid guanidinium thiocyanate-phenol-chloroform extraction. The mixture may be subjected to one or more additional RNA extraction and purification methods known in the art.

In some embodiments, where the quantitative expression of RNA molecules is desired, the use of an RNA stabilization buffer and bead beating is preferred to ensure release and limited degradation of RNA nucleic acid molecules.

In some embodiments where extraction of high molecular weight nucleic acid molecules is desired, bead beating and tissue homogenization column are avoided and phenol-chloroform-alcohol extraction is performed instead of silica column based extraction.

Metagenomics Analysis

The extracted and purified genetic material was prepared for sequencing using Illumina index adaptors and checked for sizing and quantity. Low cycle PCR was performed between 1-20 cycles for any input less then 50 ng of DNA, otherwise PCR-Free methods of library prep can be utilized for 50 ng of nucleic acid or greater. Gel purification was performed using the Qiagen Gel Purification Kit™ (Qiagen, Frederick, Md.). Clean PCR products were quantified using the Qubit™ 2.0 Fluorometer (Life Technologies, Carlsbad, Calif.). Samples were combined in equimolar amounts. Library pools were size verified using the Fragment Analyzer™ CE (Advanced Analytical Technologies Inc., Ames Iowa) and quantified using the Qubit™ High Sensitivity dsDNA kit (Life Technologies, Carlsbad, Calif.). After dilution, a 1% to 10% spike of PhiX™ V3 library control (Illumina, San Diego Calif.), pools were denatured for 5 minutes in an equal volume of 0.1 N NaOH then further diluted in Illumina's HT1 buffer. The denatured and PhiX-spiked pool was loaded on an Illumina Next Generation™ Sequencer with Illumina sequencing primers and set for between 50-550 base, paired-end or single reads.

A range from 1000 or greater reads of sequencing for short insert methods can be used for this method. Large insert methods such as Pac Bio™, Nanopore™, or other next gene sequencing methods can use <1000 sequencing reads. Bioinformatics quality filtering was performed before taxonomy assignment. Quality trimming of raw sequencing files may include removal of sequencing adaptors or indexes; trimming 3' or 5' end of reads based on quality scores (Q20>), basepairs of end, or signal intensity; removal of reads based on quality scores, GC content, or non-aligned basepairs; removal of overlapping reads at set number of base pairs. Alignment of processed sequencing files was done using a custom microbial genome database consisting of sequences from Refseg™, Greengeens™, HMP™, NCBI™, PATRIC™, or other public/private data repositories or in-house data sets. This database may be used as full genome alignment scaffold, k-mer fragment alignment, or other schemes practiced in the art of metagenomics and bioinformatics. Based off the number of sequencing reads/fragments that match the database genomes we assign a taxonomic identity that is common or unique to the organism. This identifier can be a barcode, nucleotide sequence, or some other computational tag that will associate the matching sequencing read to an organism or strain within a taxonomic group. Some identifiers will be of higher order and would identify domain, kingdom, phylum, class, order, family, or genus of the organism.

The present invention is able to identify the organism at the lowest order of strain within a species.

In embodiments the invention includes identification and/or analysis of one or more bacteria contained within our database (FIG. 10). Some selected examples are *Bacillus clausii, Bifidobacterium animalis, Pediococcus acidilactici, Acinetobacter indicus, Lactobacillus salivarius, Acinetobacter, Bacillus amyloliquefaciens, Lactobacillus helveticus, Bacillus subtilis, Lactobacillus plantarum, Bifidobacterium longum* subsp *infantis, Enterococcus hirae, Lactobacillus delbrueckii* subsp *bulgaricus, Enterococcus, Lactobacillus rhamnosus, Lactococcus lactis, Pseudomonas stutzeri, Lactobacillus acidophilus, Klebsiella* and *Enterobacter cloacae* strain.

In embodiments the invention includes identification and/or analysis of one or more yeast contained within our database (FIG. 10). Some selected examples are *Saccharomyces* sp. *Boulardii, Saccharomyces kudriavzevii, Saccharomyces pastorianus* and *Saccharomyces cerevisiae.*

In embodiments the invention includes identification and/or analysis of one or more phage or viruses contained within our database (FIG. 10). Some selected examples are *Bacillus* phage phi29, Enterobacteria phage HK022, *Lactobacillus* phage A2, *Escherichia* phage HK639, Phage cdtI, *Sclerotinia sclerotiorum* partitivirus S segment 2, *Burkholderia* phage BcepMu, *Lactococcus* prophage bIL311, *Enterococcus* phage phiFL4A and *Streptococcus* phage SM1.

Future database improvements will increase or refine the organisms that can be detected by this method.

Monitoring Probiotic Treatment

In some embodiments, the present invention may be used to monitor probiotic treatment in subjects. For example, prior to treatment with a probiotic, a sample obtained from the digestive tract of a subject may be obtained and the genetic material of the microbes therein extracted as disclosed herein and subjected to metagenomics analysis. Then during and/or after treatment with a given probiotic, a second sample may be obtained from the digestive tract of the subject and the genetic material of the microbes in the second sample extracted as disclosed herein and subjected to metagenomics analysis, the results of which are compared to the results of the metagenomics analysis of the first sample. Then, based on the comparative results, the probiotic treatment of the subject may be modified to obtain a desired population of microbes in the gut of the subject. For example, a probiotic that comprises a microbe whose amount is desired to be increased in the gut of the subject may be administered to the subject.

In some embodiments, the fecal sample may be mixed or cultured for determination of metabolomic of microbial fecal community. Metabolomic profile can then be used to determine probiotic strains that would benefit the individual. Examples of metabolomic profiles include those affecting energy metabolism, nutrient utilization, insulin resistance, adiposity, dyslipidemia, inflammation, short-chain fatty acids, organic acids, cytokines, neurotransmitters chemicals or phenotype and may include other metabolomic markers.

Microbiome Screening and Probiotic Selection

The present invention has been successfully used to determine the microbe content of a variety of commercially available probiotics. Additionally, the methods of the present invention are used to determine the microbe content of various probiotics and the microbiome content in the gut of the subject. Based on the microbiome content in the gut of the subject and any desired changes thereto, one may select one or more probiotics that contain the microbes that are desired to be increased and/or maintained in the subject's microbiome health. Where the microbiome represents a full picture of their microbiota and the organisms contained in them from bacteria, fungi, viruses, phages, and parasites. For example, using the methods described herein, a subject's gut microbiome is determined to contain 25% A and 75% B, Probiotic 1 is determined to contain 75% A and 25% B and Probiotic 2 is determined to contain 25% A and 75% B. If the subject's gut microbiome is desired to be maintained, one would select Probiotic 2 for administering to the subject. However, if the amounts of A and B in the subject's gut are desired to be 50/50, one may select both Probiotics 1 and 2 to be administered to the subject. Alternatively, one may select Probiotic 1 to be administered to the subject until the amounts of A and B in the subject's gut reaches 50/50. In some embodiments, one may custom tailor a probiotic formulation, e.g., containing equal, varying, or diverse amounts of A and B or other probiotic strains, for administration to the subject. Calculation models utilizing relative abundance of the microbes present in an individual's gut will help determine the type, dose, and cocktail of microbes to include in the probiotic. For example, if it is determined that organism A is reduced or absent compared to the general population or previous microbiome analysis, then we would provide probiotic or prebiotics that would increase the concentration of organism A. This prebiotic or probiotic may be the exact organism A or another organism what would support the grown of organism A. The dose given would consider relative abundance of organisms in the individual, performance characteristics of the prebiotic/probiotic such as growth rate, compatibility, receptors or receptor density, genes, or expression patterns, or metabolomic products.

Custom tailored probiotics may not be in equal amounts but are formulated based on relative abundance detected from the individual gut/fecal sample. These formulations are geared to modulate the microbiome to a healthy status. The healthy status of a microbiome is determined by the use of existing aggregate private and public databases such as MetaHIT™, Human Microbiome Project™, American Gut Project™, and the like. The healthy status may also be determined individually when a person has no known issues and is in good health, from a blood biomarker checkup perspective, and then has their full microbiome profile completed. After one or several microbiome signatures have been completed then the average of some/all of the microbes found can be understood for that individual and variances from that average can be accessed to determine if they are in dysbiosis. Microbiome profiles can be aggregated into groups that are then assigned a barcode for rapid bioinformatic assignment. Groups can be created by single or multiple phenotypic, diagnostic, or demographic information related to the individual from which the sample was collected from. A unique group can be determined from another group by using statistical models such as linear distance calculations, diversity values, classifiers such as C4.5 decision tree, or principal component analysis an comparing to an aggregate known population such as "normals" defined by the Human Microbiome Project or American Gut Project.

Thus, in some embodiments, the present invention may be used to screen the gut microbiome of a given subject and then custom tailor a probiotic regimen to the given subject based on the subject's gut microbiome.

Treatment of Dysbiosis

In some embodiments, the present invention may be used to restore a subject's gut flora and/or fauna to homeostasis after an event that has caused a shift in the subject's microbiota from balanced microbiome to one that is causing or may be causing negative side effects, disorders, and/or disease. Health conditions can include but is not limited to various conditions, from acne and allergies, through gastrointestinal ailments, obesity and cancer. One example of such a dysbiosis is in the case of the onset of obesity. Several strains of microbes in the guts of subjects have been shown to be associated with obesity or weight management issues suffered by the subjects. See, e.g., Ley, et al. (2005) PNAS USA 102:11070-11075. For example, in obese animal and human subjects, the ratio of Bacterides to Firmicutes phyla microbes plays an important role in metabolic performance. See, e.g., Turnbaugh, et al. (2012) PLOS ONE 7:e41079. Some gut microbes known to be associated with obesity and weight management issues include *Bacteroides uniformis, Bacteroides pectinophilus, Roseburia inulinivorans, Methanobrevibacter smithii*, and *Bifidobacterium animalis*.

Thus, in some embodiments, a ratio of a first given microbe to a second given microbe in the gut of a subject is determined using the methods described herein and then if the ratio is undesired or abnormal, the subject is administered a treatment to modify the ratio to be a desired ratio. In some embodiments, the amount of a first given microbe in a gut of a subject relative to the total amount of all the microbes in the gut of the subject is determined using the methods described herein and then if the relative amount of the first given microbe is undesired or abnormal, the subject is administered a treatment to modify the amount to be a desired amount. Such treatments include administering to the subject: a probiotic containing one or more microbes whose amounts are desired to be increased in the gut of the subject, an antimicrobial agent, e.g., an antibiotic, an antifungal, an antiviral, etc., to kill or slow the growth of a microbe or microbes whose amounts are desired to be decreased in the gut of the subject, a diet and/or a dietary supplement that supports the growth or maintenance of a healthy gut microbiome, e.g., a prebiotic, magnesium, fish oil, L-glutamine, vitamin D, etc., and the like. For example, Million, et al. ((2005) Int. J. Obes. 36:817-825) indicate that the gut microbiota of obese subjects are enriched in *Lactobacillus reuteri* and depleted in *Bifidobacterium animalis* and Methanobrevibacter *smithii*. Therefore, after determining the amounts of *Lactobacillus reuteri, Bifidobacterium animalis*, and *Methanobrevibacter smithii* in the gut of a subject using the methods described herein and finding that the amounts are typical or indicative of obesity-associated gut microbiota, the subject may be administered a probiotic containing *Bifidobacterium animalis* and Methanobrevibacter *smithii* and relatively little to no amount of *Lactobacillus reuteri*.

Scoring of Your Microbiome

Scoring of the microbiome signature overall uses a similar decision tree, algorithm, artificial intelligence, script, or logic tree as represented in table 1. This system would enable a score that helps a user understand how healthy their gut microbiome is and if they need to take action on a few or many challenges found. Challenges can include but not limited to, identification of known pathogenic organisms, count and identification of opportunistic pathogens, latent organisms known to cause pathogenic affects when given opportunity, lack of support for good microbial environment but their composition or lack of key strains, overall diversity and count of unique organisms found in top 10 and or organisms with greater than 0.1% prevalence.

Diversity cut offs were determined from an aggregate of sample analysis and a cutoff is determined at x relative abundance. For example, if x=0.1% then 352 unique organisms make up the average healthy profile. Then apply standard deviations around this number and using a Gaussian distribution and percentile under the curve analysis we can score how close to the average diversity number from our database average. The lower your diversity number and further away from the average you are then the less that microbiome would score. The higher the number and the greater your diversity is the more that microbiome would score. This type of scoring categories along with probiotic score will determine a number and visual metered score for the custom to understand how healthy their microbiome is. An example of the graphic visualization is included below. Where low is equal to low microbiome quality and high is equal to high microbiome quality and score. Low->30 out of 100, Med>65 out of 100, High=65 or greater out of 100.

An example of a scoring and probiotic formula algorithm is included in Table 1 below. Table 1 can be represented as decision tree, algorithm, artificial intelligence, script, or logic tree. The function of such decision tree, algorithm, artificial intelligence, script, or logic tree would be output a score of wellness of the individual microbiome as related to probiotics detected and to provide formulation and dosing recommendations for probiotic usage.

An exemplary list of potential categories into which microbes may be grouped is set forth in Table 2 below.

TABLE 1

Example Decision Table for Probiotic Scoring and Formulation. Includes the Utilization of a Probiotic Strain Database, Metagenomic Analysis Database, and Literature Curation Database

| Criteria Number | Criteria | Criteria Answer | Score or Inclusion/Exclusion |
|---|---|---|---|
| 1 | Greater than 100 reads | Yes | If yes then include |
| 2 | Greater than 50% of total probiotic reads | Yes | |
| 3 | Greater than 10,000 reads | Yes | If yes do not include in probiotic formula |
| 4 | Greater than 50% of total reads | No | |
| 5 | Greater than 30,000 reads | Yes | If yes do not include in probiotic formula |
| 6 | Greater than 30,000 reads for x number of probiotics | Yes | If $x > 5$ then score +20, $x > 3$ score 10, $x > 1$ score 5 |
| 7 | Total number of microbes above 100 reads (count) | x | If $x > 10$ then score +20, $x > 10$ then score 10, $x > 5$ score 5 |
| 8 | Query for probiotic strains and output where 1 = yes and 4 is no and 6 is no and the number of reads is less than 1000 | Yes | Include in formula at 20 CFU/g or greater |
| 9 | If *bacillus* | Yes | Do not include |
| 10 | If *lactobacillus acidophilus* greater than x reads | Yes | If $x > 10000$ score +20, if $x > 1000$ score +10, if $x > 100$ score +5 |
| 11 | If *bacillus* genus greater than x reads | Yes | If $x > 1000$ score +20, if $x > 100$ score +10, if $x > 10$ score +5 |
| 12 | If *Saccharomyes boulardi* greater than x reads | Yes | If $x > 1000$ score +20, if $x > 100$ score +10, if $x > 10$ score +5 |
| 13 | If infant if nursing and *bifidobacterium infantis* > x % | Yes | If $x > 10$ then score +5, $x > 30\%$ then score +10, $x > 50\%$ then score +20, $x > 70\%$ then score +30 |
| 14 | If not infant, not child and *bifidobacterium infantis* > x % | Yes | If $x > 20$ then score +5, if $x > 10$ then score +10, if $x < 10$ then score +20 |
| 15 | Query to probiotic function, if function table is equal to health phenotype or healthDx then include in formula unless 3 or 5 = yes | | |

TABLE 2

Potential Categories from which to Create Groups

| Categories1 | Categories2 |
|---|---|
| ACID_REFLUX | FLOSSING_FREQUENCY |
| ACNE_MEDICATION | FLU_VACCINE_DATE |
| ACNE_MEDICATION_OTC | FROZEN_DESSERT_FREQUENCY |
| ADD_ADHD | FRUIT_FREQUENCY |
| AGE_CAT | FUNGAL_OVERGROWTH |
| AGE_CORRECTED | GEO_LOC_NAME |
| AGE_YEARS | GLUTEN |
| ALCOHOL_CONSUMPTION | HAS_PHYSICAL_SPECIMEN |
| ALCOHOL_FREQUENCY | HEIGHT_CM |
| ALCOHOL_TYPES | HEIGHT_UNITS |
| ALCOHOL_TYPES_BEERCIDER | HIGH_FAT_RED_MEAT_FREQUENCY |
| ALCOHOL_TYPES_RED_WINE | HOMECOOKED_MEALS_FREQUENCY |
| ALCOHOL_TYPES_SOUR_BEERS | HOST_COMMON_NAME |
| ALCOHOL_TYPES_SPIRITSHARD_ALCOHOL | HOST_SUBJECT_ID |
| ALCOHOL_TYPES_UNSPECIFIED | HOST_TAXID |
| ALCOHOL_TYPES_WHITE_WINE | IBD |
| ALLERGIC_TO | IBD_DIAGNOSIS |
| ALLERGIC_TO_I_HAVE_NO_FOOD_ALLERGIES_THAT_I_KNOW_OF | IBD_DIAGNOSIS_REFINED |
| ALLERGIC_TO_OTHER | IBS |
| ALLERGIC_TO_PEANUTS | INSTRUMENT_MODEL |
| ALLERGIC_TO_SHELLFISH | KIDNEY_DISEASE |
| ALLERGIC_TO_TREE_NUTS | LACTOSE |
| ALLERGIC_TO_UNSPECIFIED | LAST_MOVE |
| ALTITUDE | LAST_TRAVEL |
| ALZHEIMERS | LATITUDE |
| ANONYMIZED_NAME | LEVEL_OF_EDUCATION |
| ANTIBIOTIC_HISTORY | LIBRARY_CONSTRUCTION_PROTOCOL |
| APPENDIX_REMOVED | LINKER |
| ARTIFICIAL_SWEETENERS | LinkerPrimerSequence |
| ASD | LIVER_DISEASE |
| ASSIGNED_FROM_GEO | LIVINGWITH |
| AUTOIMMUNE | LONGITUDE |
| BarcodeSequence | LOWGRAIN_DIET_TYPE |
| BIRTH_YEAR | LUNG_DISEASE |
| BMI | MASTERMIX_LOT |
| BMI_CAT | MEAT_EGGS_FREQUENCY |
| BMI_CORRECTED | MENTAL_ILLNESS |
| BODY_HABITAT | MENTAL_ILLNESS_TYPE |
| BODY_PRODUCT | MENTAL_ILLNESS_TYPE_ANOREXIA_NERVOSA |
| BODY_SITE | MENTAL_ILLNESS_TYPE_BIPOLAR_DISORDER |
| BOWEL_MOVEMENT_FREQUENCY | MENTAL_ILLNESS_TYPE_BULIMIA_NERVOSA |
| BOWEL_MOVEMENT_QUALITY | MENTAL_ILLNESS_TYPE_DEPRESSION |
| BREASTMILK_FORMULA_ENSURE | MENTAL_ILLNESS_TYPE_PTSD_POSTTRAUMATIC_STRESS_DISORDER |
| CANCER | MENTAL_ILLNESS_TYPE_SCHIZOPHRENIA |
| CANCER_TREATMENT | MENTAL_ILLNESS_TYPE_SUBSTANCE_ABUSE |
| CARDIOVASCULAR_DISEASE | MENTAL_ILLNESS_TYPE_UNSPECIFIED |
| CAT | MIGRAINE |

TABLE 2-continued

Potential Categories from which to Create Groups

| | |
|---|---|
| CDIFF | MILK_CHEESE_FREQUENCY |
| CENSUS_REGION | MILK_SUBSTITUTE_FREQUENCY |
| CENTER_NAME | MULTIVITAMIN |
| CENTER_PROJECT_NAME | NAIL_BITER |
| chao1_10k | NON_FOOD_ALLERGIES |
| chao1_1k | NON_FOOD_ALLERGIES_BEESTINGS |
| CHICKENPOX | NON_FOOD_ALLERGIES_DRUG_EG_PENICILLIN |
| CLINICAL_CONDITION | NON_FOOD_ALLERGIES_PET_DANDER |
| COLLECTION_DATE | NON_FOOD_ALLERGIES_POISON_IVYOAK |
| COLLECTION_MONTH | NON_FOOD_ALLERGIES_SUN |
| COLLECTION_SEASON | NON_FOOD_ALLERGIES_UNSPECIFIED |
| COLLECTION_TIME | observed_otus_10k |
| COLLECTION_TIMESTAMP | observed_otus_1k |
| COMMON_NAME | OLIVE_OIL |
| CONSUME_ANIMAL_PRODUCTS_ABX | ONE_LITER_OF_WATER_A_DAY_FREQUENCY |
| CONTRACEPTIVE | ORIG_NAME |
| COSMETICS_FREQUENCY | OTHER_SUPPLEMENT_FREQUENCY |
| COUNTRY | PCR_PRIMERS |
| COUNTRY_OF_BIRTH | PD_whole_tree_10k |
| COUNTRY_RESIDENCE | PD_whole_tree_1k |
| CSECTION | PETS_OTHER |
| DEODORANT_USE | PETS_OTHER_FREETEXT |
| DEPRESSION_BIPOLAR_SCHIZOPHRENIA | PHYSICAL_SPECIMEN_LOCATION |
| DEPTH | PHYSICAL_SPECIMEN_REMAINING |
| Description | PKU |
| DIABETES | PLATFORM |
| DIABETES_TYPE | PLATING |
| DIET_TYPE | POULTRY_FREQUENCY |
| DNA_EXTRACTED | POOL_FREQUENCY |
| DOG | PREGNANT |
| DOMINANT_HAND | PREPARED_MEALS_FREQUENCY |
| DRINKING_WATER_SOURCE | PRIMER_DATE |
| DRINKS_PER_SESSION | PRIMER_PLATE |
| ECONOMIC_REGION | PROBIOTIC_FREQUENCY |
| ELEVATION | PROCESSING_ROBOT |
| ENA-BASE-COUNT | PROJECT_NAME |
| ENA-CHECKLIST | PUBLIC |
| ENA-SPOT-COUNT | QIITA_PREP_ID |
| ENV_BIOME | QIITA_STUDY_ID |
| ENV_FEATURE | RACE |
| ENV_MATERIAL | READY_TO_EAT_MEALS_FREQUENCY |
| ENV_MATTER | RED_MEAT_FREQUENCY |
| ENV_PACKAGE | REQUIRED_SAMPLE_INFO_STATUS |
| EPILEPSY_OR_SEIZURE_DISORDER | ROOMMATES |
| EXERCISE_FREQUENCY | ROOMMATES_IN_STUDY |
| EXERCISE_LOCATION | RUN_CENTER |
| EXPERIMENT_CENTER | RUN_DATE |
| EXPERIMENT_DESIGN_DESCRIPTION | RUN_PREFIX |
| EXPERIMENT_TITLE | SALTED_SNACKS_FREQUENCY |
| EXTRACTIONKIT_LOT | #Sample ID |
| EXTRACTION_ROBOT | SAMPLE_PLATE |

TABLE 2-continued

Potential Categories from which to Create Groups

| Categories3 | Categories4 |
|---|---|
| FED_AS_INFANT | SAMPLE_TYPE |
| FERMENTED_PLANT_FREQUENCY | SAMP_SIZE |
| SCIENTIFIC_NAME | VIOSCREEN_D_YOGURT |
| SEAFOOD_FREQUENCY | VIOSCREEN_EER |
| SEASONAL_ALLERGIES | VIOSCREEN_EMAIL |
| SEQUENCING_METH | VIOSCREEN_ERYTHR |
| SEX | VIOSCREEN_FAT |
| shannon_10k | VIOSCREEN_F_CITMLB |
| shannon_1k | VIOSCREEN_FIBER |
| SIBO | VIOSCREEN_FIBH2O |
| SKIN_CONDITION | VIOSCREEN_FIBINSO |
| SLEEP_DURATION | VIOSCREEN_FINISHED |
| SMOKING_FREQUENCY | VIOSCREEN_FISH_SERVINGS |
| SOFTENER | VIOSCREEN_F_NJ_CITMLB |
| SPECIALIZED_DIET | VIOSCREEN_F_NJ_OTHER |
| SPECIALIZED_DIET_EXCLUDE_DAIRY | VIOSCREEN_F_NJ_TOTAL |
| SPECIALIZED_DIET_EXCLUDE_NIGHTSHADES | VIOSCREEN_FOL_DEQV |
| SPECIALIZED_DIET_EXCLUDE_REFINED_SUGARS | VIOSCREEN_FOL_NAT |
| SPECIALIZED_DIET_FODMAP | VIOSCREEN_FOL_SYN |
| SPECIALIZED_DIET_HALAAL | VIOSCREEN_FORMONTN |
| SPECIALIZED_DIET_I_DO_NOT_EAT_A_SPECIALIZED_DIET | VIOSCREEN_F_OTHER |
| SPECIALIZED_DIET_KOSHER | VIOSCREEN_FRIED_FISH_SERVINGS |
| SPECIALIZED_DIET_MODIFIED_PALEO_DIET | VIOSCREEN_FRIED_FOOD_SERVINGS |
| SPECIALIZED_DIET_OTHER_RESTRICTIONS_NOT_DESCRIBED_HERE | VIOSCREEN_FRT5_DAY |
| SPECIALIZED_DIET_PALEODIET_OR_PRIMAL_DIET | VIOSCREEN_FRTSUMM |
| SPECIALIZED_DIET_RAW_FOOD_DIET | VIOSCREEN_FRUCTOSE |
| SPECIALIZED_DIET_UNSPECIFIED | VIOSCREEN_FRUIT_SERVINGS |
| SPECIALIZED_DIET_WESTENPRICE_OR_OTHER_LOWGRAIN_LOW_PROCESSED | VIOSCREEN_F_TOTAL |
| STATE | VIOSCREEN_GALACTOS |
| SUBSET_AGE | VIOSCREEN_GAMMTOCO |
| SUBSET_ANTIBIOTIC_HISTORY | VIOSCREEN_GENDER |
| SUBSET_BMI | VIOSCREEN_GENISTN |
| SUBSET_DIABETES | VIOSCREEN_GLAC |
| SUBSET_HEALTHY | VIOSCREEN_GLTC |
| SUBSET_IBD | VIOSCREEN_GLUCOSE |
| SUGAR_SWEETENED_DRINK_FREQUENCY | VIOSCREEN_GLUTAMIC |
| SUGARY_SWEETS_FREQUENCY | VIOSCREEN_GLYCINE |
| SURVEY_ID | VIOSCREEN_GLYCITN |
| TARGET_GENE | VIOSCREEN_G_NWHL |
| TARGET_SUBFRAGMENT | VIOSCREEN_GRAMS |
| TAXON_ID | VIOSCREEN_G_TOTAL |
| TEETHBRUSHING_FREQUENCY | VIOSCREEN_G_WHL |
| THYROID | VIOSCREEN_HEI2010_DAIRY |
| TITLE | VIOSCREEN_HEI2010_EMPTY_CALORIES |
| TM1000_8_TOOL | VIOSCREEN_HEI2010_FATTY_ACIDS |
| TM300_8_TOOL | VIOSCREEN_HEI2010_FRUIT |
| TM50_8_TOOL | VIOSCREEN_HEI2010_GREENS_BEANS |
| TONSILS_REMOVED | VIOSCREEN_HEI2010_PROTIEN_FOODS |

TABLE 2-continued

Potential Categories from which to Create Groups

| | |
|---|---|
| TYPES_OF_PLANTS | VIOSCREEN_HEI2010_REFINED_GRAINS |
| VEGETABLE_FREQUENCY | VIOSCREEN_HEI2010_SCORE |
| VIOSCREEN_A_BEV | VIOSCREEN_HEI2010_SEA_FOODS_PLANT_PROTIENS |
| VIOSCREEN_A_CAL | VIOSCREEN_HEI2010_SODIUM |
| VIOSCREEN_ACESUPOT | VIOSCREEN_HEI2010_VEG |
| VIOSCREEN_ACTIVITY_LEVEL | VIOSCREEN_HEI2010_WHOLE_FRUIT |
| VIOSCREEN_ADD_SUG | VIOSCREEN_HEI2010_WHOLE_GRAINS |
| VIOSCREEN_ADDSUGAR | VIOSCREEN_HEI_DRK_G_ORG_VEG_LEG |
| VIOSCREEN_ADSUGTOT | VIOSCREEN_HEI_FRUIT |
| VIOSCREEN_AGE | VIOSCREEN_HEIGHT |
| VIOSCREEN_ALANINE | VIOSCREEN_HEI_GRAINS |
| VIOSCREEN_ALCOHOL | VIOSCREEN_HEI_MEAT_BEANS |
| VIOSCREEN_ALCOHOL_SERVINGS | VIOSCREEN_HEI_MILK |
| VIOSCREEN_ALPHACAR | VIOSCREEN_HEI_NON_JUICE_FRT |
| VIOSCREEN_ALPHTOCE | VIOSCREEN_HEI_OILS |
| VIOSCREEN_ALPHTOCO | VIOSCREEN_HEI_SAT_FAT |
| VIOSCREEN_ARGININE | VIOSCREEN_HEI_SCORE |
| VIOSCREEN_ASH | VIOSCREEN_HEI_SODIUM |
| VIOSCREEN_ASPARTAM | VIOSCREEN_HEI_SOL_FAT_ALC_ADD_SUG |
| VIOSCREEN_ASPARTIC | VIOSCREEN_HEI_VEG |
| VIOSCREEN_AVCARB | VIOSCREEN_HEI_WHL_GRAINS |
| VIOSCREEN_BCODEID | VIOSCREEN_HISTIDIN |
| VIOSCREEN_BETACAR | VIOSCREEN_INOSITOL |
| VIOSCREEN_BETACRYP | VIOSCREEN_IRON |
| VIOSCREEN_BETAINE | VIOSCREEN_ISOLEUC |
| VIOSCREEN_BETATOCO | VIOSCREEN_ISOMALT |
| VIOSCREEN_BIOCHANA | VIOSCREEN_JOULES |
| VIOSCREEN_BMI | VIOSCREEN_JUICE_SERVINGS |
| VIOSCREEN_CAFFEINE | VIOSCREEN_LACTITOL |
| VIOSCREEN_CALCIUM | VIOSCREEN_LACTOSE |
| VIOSCREEN_CALCIUM_AVG | VIOSCREEN_LEGUMES |
| VIOSCREEN_CALCIUM_DOSE | VIOSCREEN_LEUCINE |
| VIOSCREEN_CALCIUM_FREQ | VIOSCREEN_LINE_GI |
| VIOSCREEN_CALCIUM_FROM_DAIRY_SERVINGS | VIOSCREEN_LOW_FAT_DAIRY_SERVING |
| VIOSCREEN_CALCIUM_SERVINGS | VIOSCREEN_LUTZEAX |
| VIOSCREEN_CALORIES | VIOSCREEN_LYCOPENE |
| VIOSCREEN_CARBO | VIOSCREEN_LYSINE |
| VIOSCREEN_CHOLEST | VIOSCREEN_MAGNES |
| VIOSCREEN_CHOLINE | VIOSCREEN_MALTITOL |
| VIOSCREEN_CLAC9T11 | VIOSCREEN_MALTOSE |
| VIOSCREEN_CLAT10C12 | VIOSCREEN_MANGAN |
| VIOSCREEN_COPPER | VIOSCREEN_MANNITOL |
| VIOSCREEN_COUMEST | VIOSCREEN_M_EGG |
| VIOSCREEN_CYSTINE | VIOSCREEN_METHHIS3 |

TABLE 2-continued

Potential Categories from which to Create Groups

| | |
|---|---|
| VIOSCREEN_DAIDZEIN | VIOSCREEN_METHION |
| VIOSCREEN_DATABASE | VIOSCREEN_MFA141 |
| VIOSCREEN_D_CHEESE | VIOSCREEN_MFA161 |
| VIOSCREEN_DELTTOCO | VIOSCREEN_MFA181 |
| VIOSCREEN_DISCFAT_OIL | VIOSCREEN_MFA201 |
| VIOSCREEN_DISCFAT_SOL | VIOSCREEN_MFA221 |
| VIOSCREEN_D_MILK | VIOSCREEN_MFATOT |
| VIOSCREEN_D_DOB | VIOSCREEN_M_FISH_HI |
| VIOSCREEN_D_TOTAL | VIOSCREEN_M_FISH_LO |
| VIOSCREEN_D_TOT_SOYM | VIOSCREEN_M_FRANK |

| Categories5 | Categories6 |
|---|---|
| VIOSCREEN_M_MEAT | VIOSCREEN_VITB12 |
| VIOSCREEN_M_MPF | VIOSCREEN_VITB6 |
| VIOSCREEN_M_NUTSD | VIOSCREEN_VITC |
| VIOSCREEN_M_ORGAN | VIOSCREEN_VITD |
| VIOSCREEN_M_POULT | VIOSCREEN_VITD2 |
| VIOSCREEN_M_SOY | VIOSCREEN_VITD3 |
| VIOSCREEN_MULTI_CALCIUM_AVG | VIOSCREEN_VITD_IU |
| VIOSCREEN_MULTI_CALCIUM_DOSE | VIOSCREEN_VITE_IU |
| VIOSCREEN_MULTIVITAMIN | VIOSCREEN_VITK |
| VIOSCREEN_MULTIVITAMIN_FREQ | VIOSCREEN_V_ORANGE |
| VIOSCREEN_NATOCO | VIOSCREEN_V_OTHER |
| VIOSCREEN_NCCGLBR | VIOSCREEN_V_POTATO |
| VIOSCREEN_NCCGLGR | VIOSCREEN_V_STARCY |
| VIOSCREEN_NIACIN | VIOSCREEN_V_TOMATO |
| VIOSCREEN_NIACINEQ | VIOSCREEN_V_TOTAL |
| VIOSCREEN_NITROGEN | VIOSCREEN_WATER |
| VIOSCREEN_NON_FRIED_FISH_SERVINGS | VIOSCREEN_WEIGHT |
| VIOSCREEN_NUTRIENT_RECOMMENDATION | VIOSCREEN_WGRAIN |
| VIOSCREEN_OMEGA3 | VIOSCREEN_WHOLE_GRAIN_SERVINGS |
| VIOSCREEN_OXALIC | VIOSCREEN_XYLITOL |
| VIOSCREEN_OXALICM | VIOSCREEN_ZINC |
| VIOSCREEN_PANTOTHE | VITAMIN_B_SUPPLEMENT_FREQUENCY |
| VIOSCREEN_PECTINS | VITAMIN_D_SUPPLEMENT_FREQUENCY |
| VIOSCREEN_PFA182 | VIVID_DREAMS |
| VIOSCREEN_PFA183 | WATER_LOT |
| VIOSCREEN_PFA184 | WEIGHT_CHANGE |
| VIOSCREEN_PFA204 | WEIGHT_KG |
| VIOSCREEN_PFA205 | WEIGHT_UNITS |
| VIOSCREEN_PFA225 | WELL_DESCRIPTION |
| VIOSCREEN_PFA226 | WELL_ID |
| VIOSCREEN_PFATOT | WHOLE_EGGS |
| VIOSCREEN_PHENYLAL | WHOLE_GRAIN_FREQUENCY |
| VIOSCREEN_PHOSPHOR | |
| VIOSCREEN_PHYTIC | |
| VIOSCREEN_PINITOL | |
| VIOSCREEN_POTASS | |
| VIOSCREEN_PROCDATE | |

TABLE 2-continued

Potential Categories from which to Create Groups

VIOSCREEN_PROLINE
VIOSCREEN_PROTANIM
VIOSCREEN_PROTEIN
VIOSCREEN_PROTOCOL
VIOSCREEN_PROTVEG
VIOSCREEN_QUESTIONNAIRE
VIOSCREEN_RECNO
VIOSCREEN_RETINOL
VIOSCREEN_RGRAIN
VIOSCREEN_RIBOFLA
VIOSCREEN_SACCHAR
VIOSCREEN_SALAD_VEGETABLE_SERVINGS
VIOSCREEN_SATOCO
VIOSCREEN_SCF
VIOSCREEN_SCFV
VIOSCREEN_SELENIUM
VIOSCREEN_SERINE
VIOSCREEN_SFA100
VIOSCREEN_SFA120
VIOSCREEN_SFA140
VIOSCREEN_SFA160
VIOSCREEN_SFA170
VIOSCREEN_SFA180
VIOSCREEN_SFA200
VIOSCREEN_SFA220
VIOSCREEN_SFA40
VIOSCREEN_SFA60
VIOSCREEN_SFA80
VIOSCREEN_SFATOT
VIOSCREEN_SODIUM
VIOSCREEN_SORBITOL
VIOSCREEN_SRVID
VIOSCREEN_STARCH
VIOSCREEN_STARTED
VIOSCREEN_SUBJECT_ID
VIOSCREEN_SUCPOLY
VIOSCREEN_SUCRLOSE

TABLE 2-continued

Potential Categories from which to Create Groups

VIOSCREEN_SUCROSE
VIOSCREEN_SWEET_SERVINGS
VIOSCREEN_TAGATOSE
VIOSCREEN_TFA161T
VIOSCREEN_TFA181T
VIOSCREEN_TFA182T
VIOSCREEN_TGRAIN
VIOSCREEN_THIAMIN
VIOSCREEN_THREONIN
VIOSCREEN_TIME
VIOSCREEN_TOTALTFA
VIOSCREEN_TOTCLA
VIOSCREEN_TOTFOLAT
VIOSCREEN_TOTSUGAR
VIOSCREEN_TRYPTOPH
VIOSCREEN_TYROSINE
VIOSCREEN_USER_ID
VIOSCREEN_VALINE
VIOSCREEN_V_DRKGR
VIOSCREEN_VEG5_DAY
VIOSCREEN_VEGETABLE_SERVINGS
VIOSCREEN_VEGSUMM
VIOSCREEN_VISIT
VIOSCREEN_VITA_IU
VIOSCREEN_VITA_RAE
VIOSCREEN_VITA_RE

All scientific and technical terms used in this application have meanings commonly used in the art unless otherwise specified.

As used herein, the term "subject" includes humans and non-human animals. The term "non-human animal" includes all vertebrates, e.g., mammals and non-mammals, such as non-human primates, horses, sheep, dogs, cows, pigs, chickens, and other veterinary subjects and test animals.

The use of the singular can include the plural unless specifically stated otherwise. As used in the specification and the appended claims, the singular forms "a", "an", and "the" can include plural referents unless the context clearly dictates otherwise. The use of "or" can mean "and/or" unless stated otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

As used herein, the terms "sample" and "biological sample" refer to any sample suitable for the methods provided by the present invention. A sample of cells can be any sample, including, for example, gut or fecal sample obtained by non-invasive or invasive techniques such as biopsy of a subject. In one embodiment, the term "sample" refers to any preparation derived from fecal matter or gut tissue of a subject. For example, a sample of cells obtained using the non-invasive method described herein can be used to isolate nucleic acid molecules or proteins for the methods of the present invention.

In embodiments, analysis can be of any nucleic acid, including DNA, RNA, cDNA, miRNA, mtDNA, single or double-stranded. This nucleic acid can be of any length, as short as oligos of about 5 bp to as long a megabase or even longer. As used herein, the term "nucleic acid molecule" means DNA, RNA, single-stranded, double-stranded or triple stranded and any chemical modifications thereof. Virtually any modification of the nucleic acid is contemplated. A "nucleic acid molecule" can be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000, 000, 1,500,000, 2,000,000, 5,000,000 or even more bases in length, up to a full-length chromosomal DNA molecule. For methods that analyze expression of a gene, the nucleic acid isolated from a sample is typically RNA.

A single-stranded nucleic acid molecule is "complementary" to another single-stranded nucleic acid molecule when it can base-pair (hybridize) with all or a portion of the other nucleic acid molecule to form a double helix (double-stranded nucleic acid molecule), based on the ability of guanine (G) to base pair with cytosine (C) and adenine (A) to base pair with thymine (T) or uridine (U). For example, the nucleotide sequence 5'-TATAC-3' is complementary to the nucleotide sequence 5'-GTATA-3'.

As used herein "hybridization" refers to the process by which a nucleic acid strand joins with a complementary strand through base pairing. Hybridization reactions can be sensitive and selective so that a particular sequence of interest can be identified even in samples in which it is present at low concentrations. In an in vitro situation, suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature. For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 mg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

As used herein, the term "microbiome" refers to microorganisms, including bacteria, viruses, and fungi, archaea, protozoa, amoeba, or helminths that inhabit the gut of the subject.

As used herein, the terms microbial, microbe, or microorganism refer to any microscopic organism including prokaryotes or eukaryotes, spores, bacterium, archeaebacterium, fungus, virus, or protist, unicellular or multicellular.

The present invention is described partly in terms of functional components and various processing steps. Such functional components and processing steps may be realized by any number of components, operations and techniques configured to perform the specified functions and achieve the various results. For example, the present invention may employ various biological samples, biomarkers, elements, materials, computers, data sources, storage systems and media, information gathering techniques and processes, data processing criteria, statistical analyses, regression analyses and the like, which may carry out a variety of functions. In addition, although the invention is described in the medical diagnosis context, the present invention may be practiced in conjunction with any number of applications, environments and data analyses; the systems described herein are merely exemplary applications for the invention.

Methods for data analysis according to various aspects of the present invention may be implemented in any suitable manner, for example using a computer program operating on the computer system. An exemplary analysis system, according to various aspects of the present invention, may be implemented in conjunction with a computer system, for example a conventional computer system comprising a processor and a random access memory, such as a remotely-accessible application server, network server, personal computer or workstation. The computer system also suitably includes additional memory devices or information storage systems, such as a mass storage system and a user interface, for example a conventional monitor, keyboard and tracking device. The computer system may, however, comprise any suitable computer system and associated equipment and may be configured in any suitable manner. In one embodiment, the computer system comprises a stand-alone system. In another embodiment, the computer system is part of a network of computers including a server and a database.

The software required for receiving, processing, and analyzing genetic information may be implemented in a single device or implemented in a plurality of devices. The software may be accessible via a network such that storage and processing of information takes place remotely with respect to users. The analysis system according to various aspects of the present invention and its various elements provide functions and operations to facilitate microbiome analysis, such as data gathering, processing, analysis, reporting and/or diagnosis. The present analysis system maintains information relating to microbiomes and samples and facilitates analysis and/or diagnosis. For example, in the present embodiment, the computer system executes the computer program, which may receive, store, search, analyze, and report information relating to the microbiome. The computer program may comprise multiple modules performing various functions or operations, such as a processing module for processing raw data and generating supplemental data and an analysis module for analyzing raw data and supplemental data to generate a models and/or predictions.

The analysis system may also provide various additional modules and/or individual functions. For example, the analysis system may also include a reporting function, for example to provide information relating to the processing and analysis functions. The analysis system may also provide various administrative and management functions, such as controlling access and performing other administrative functions.

To the extent necessary to understand or complete the disclosure of the present invention, all publications, patents, and patent applications mentioned herein are expressly incorporated by reference therein to the same extent as though each were individually so incorporated.

Although the invention has been described with reference to the above example, it will be understood that modifications and variations are encompassed within the spirit and scope of the invention. Accordingly, the invention is limited only by the following claims.

What is claimed is:

1. A method comprising:
   extracting genetic material from any microbes present in a first sample obtained from the subject by: i) mixing the sample with a first lysis solution comprising a detergent, and a chelator; ii) adding a second lysis solution having a lysozyme to the mixture of step i); and iii) adding a third lysis solution comprising a chaotropic agent, to the mixture of step ii);
   subjecting the genetic material extracted from the first sample to metagenomics analysis;
   diagnosing the subject as having dysbiosis based on the metagenomics analysis of the first sample;
   administering a probiotic to the subject to treat the dysbiosis;
   extracting genetic material from any microbes present in a second sample obtained from the subject in the same manner as the extraction of genetic material from the first sample;
   performing metagenomics analysis on the extracted genetic material from the second sample; and
   assessing effectiveness of the dysbiosis treatment; and
   administering a modified probiotic which is formulated specifically to the dysbiosis in the subject and based on the assessment of effectiveness, to the subject to treat the dysbiosis.

2. The method of claim 1, wherein the probiotic treatment modifies the microbe population within the subject.

3. The method of claim 1, further comprising analysis of metabolomic markers to determine appropriate probiotic treatment.

4. The method of claim 1, wherein probiotic treatment follows use of an antibiotic, chemotherapy, a pharmaceutical, environmental change, traveling, contaminate digestions, infarction of the intestines or gut, stress, or other effect which disruption of the microbial population can occur.

5. The method of claim 2, wherein modulation of the microbiome is to return an individual to a previous population of microbes of when the individual was known to be healthy.

6. The method of claim 2, wherein modulation of the microbiome by a probiotic and/or a prebiotic is to restore microbiome profile to a normal gut that has been defined either internally by a database or externally by a public database.

7. The method of claim 6, wherein normal is defined as similar to the microbiome profile of a fecal matter repository sample used in fecal matter transplants, but used as a probiotic/prebiotic to restore a dysbiosis.

8. The method of claim 1, wherein metagenomic analysis comprises use of a database having genomic data of organisms useful for identification of such organisms.

9. The method of claim 8, wherein the database may be processed as whole genomes, k-mers of various lengths that are common to a higher order and unique to a specific one, or other means of barcoding genomes to match them to sequencing results.

10. The method of claim 1, wherein metagenomic analysis comprises preprocessing of sequencing information selected from removing duplicates, removing adaptor sequencing, removing 5' or 3' sequencing to improve the quality of base calling, filtering human reads, creating paired reads or separating them, and limiting overlap of reads.

11. The method of claim 8, wherein metagenomic analysis comprises aligning sequencing information to the database by use of a software or system where the sequencing information may be broken into k-mers of particular length, used as full fragments, be scaffolded and aligned to a large reference genome, or other method to create a report of organisms identified, relative abundance of organism identified, genome size, total fragments aligned, unique fragments aligned at the strain, species, genus, family, order, class, phylum, kingdom, or domain.

12. The method of claim 1, wherein microbiome profiles enable identification of a disease, disorder, or specific signature indicating a dysbiosis where probiotic and/or dietary supplement treatment can be applied to modulate the microbiome to improve the underlying profile.

13. The method of claim 12, wherein a group is created based on demographic, phenotypic, or diagnostic information and a barcode assigned to that group of profiles.

14. The method of claim 13, wherein statistical analysis is used to determine how closely related the individual microbiome profile is to an known group in a database.

15. A computing system comprising: a memory; and one or more processors coupled to the memory, the one or more processors configured to perform operations to perform the method according to claim 1.

16. The method of claim 1, wherein genetic material is extracted from microbes including bacteria, archaea, fungi, protozoa, helminths, parasites, viruses, phages, spores, and algae.

17. The method of claim 1, further comprising identifying a disease or disorder in the subject based on the dysbiosis.

18. The method of claim 17, further comprising administering a therapy to the subject to treat the disease or disorder, wherein the disease or disorder is acne, allergy, gastrointestinal disorder, obesity or cancer.

19. The method of claim 18, wherein the disease or disorder is obesity.

20. The method of claim 19, wherein the therapy comprises Bifidobacterium animalis or Methanobrevibacter smithii.

* * * * *